(12) United States Patent
Bursac et al.

(10) Patent No.: US 9,707,082 B2
(45) Date of Patent: Jul. 18, 2017

(54) ASSEMBLED CARTILAGE REPAIR GRAFT

(71) Applicant: RTI Surgical, Inc., Alachua, FL (US)

(72) Inventors: Predrag Bursac, Gainesville, FL (US);
Lauren M. Brown, Houston, TX (US);
Eric J. Schmitt, Gainesville, FL (US);
Guy B. Grover, Gainesville, FL (US)

(73) Assignee: RTI Surgical, Inc., Alachua, FL (US)

( * ) Notice: Subject to any disclaimer, the term of this patent is extended or adjusted under 35 U.S.C. 154(b) by 0 days.

(21) Appl. No.: 14/246,930

(22) Filed: Apr. 7, 2014

(65) Prior Publication Data

US 2014/0222159 A1    Aug. 7, 2014

Related U.S. Application Data

(63) Continuation of application No. 12/140,210, filed on Jun. 16, 2008, now abandoned.

(51) Int. Cl.
*A61F 2/30* (2006.01)
*A61F 2/28* (2006.01)
*A61B 17/86* (2006.01)

(52) U.S. Cl.
CPC .......... *A61F 2/30771* (2013.01); *A61F 2/28* (2013.01); *A61F 2/30756* (2013.01); *A61B 17/86* (2013.01); *A61F 2002/302* (2013.01); *A61F 2002/30057* (2013.01); *A61F 2002/30075* (2013.01); *A61F 2002/30138* (2013.01); *A61F 2002/30224* (2013.01); *A61F 2002/30233* (2013.01); *A61F 2002/30299* (2013.01); *A61F 2002/30332* (2013.01); *A61F 2002/30337* (2013.01); *A61F 2002/30485* (2013.01); *A61F 2002/30751* (2013.01); *A61F 2002/30766* (2013.01); *A61F 2002/30772* (2013.01); *A61F 2002/30878* (2013.01); *A61F 2002/30883* (2013.01); *A61F 2002/30929* (2013.01); *A61F 2220/0025* (2013.01); *A61F 2220/0033* (2013.01); *A61F 2230/0017* (2013.01); *A61F 2230/0065* (2013.01); *A61F 2230/0069* (2013.01); *A61F 2230/0093* (2013.01)

(58) Field of Classification Search
CPC .. A61F 2002/30751; A61F 2002/30766; A61F 2002/30759; A61F 2002/30761; A61F 2002/30057

See application file for complete search history.

(56) References Cited

U.S. PATENT DOCUMENTS

| 4,932,973 | A | 6/1990 | Gendler |
| 6,090,998 | A | 7/2000 | Grooms et al. |
| 6,200,347 | B1 | 3/2001 | Anderson |
| 6,562,073 | B2 | 5/2003 | Foley |

(Continued)

FOREIGN PATENT DOCUMENTS

| WO | WO 99/21497 A1 * | 5/1999 | ............ A61B 17/56 |
| WO | 00/54821 | 9/2000 | |

OTHER PUBLICATIONS

Bacterin Int'l, Inc., Osteowrap product web page, Jun. 2, 2008, http://www.bacterin.com/products-osteowrap.php?category=products&secondary=OsteoWrap%99.

(Continued)

*Primary Examiner* — David H Willse
(74) *Attorney, Agent, or Firm* — McAndrews, Held and Malloy

(57) ABSTRACT

Bifunctional and assembled implants are provided for osteochondral implantation.

11 Claims, 19 Drawing Sheets

(56) References Cited

U.S. PATENT DOCUMENTS

| | | | |
|---|---|---|---|
| 6,613,278 B1* | 9/2003 | Mills et al. | 422/33 |
| 6,652,593 B2 | 11/2003 | Boyer, II et al. | |
| 6,767,369 B2 | 7/2004 | Boyer, II et al. | |
| 7,044,968 B1 | 5/2006 | Yaccarino et al. | |
| 7,291,169 B2 | 11/2007 | Hodorek | |
| 2001/0020188 A1 | 9/2001 | Sander | |
| 2001/0031254 A1 | 10/2001 | Bianchi et al. | |
| 2002/0106393 A1 | 8/2002 | Bianchi et al. | |
| 2004/0078078 A1* | 4/2004 | Shepard | A61F 2/447 623/17.11 |
| 2004/0102850 A1* | 5/2004 | Shepard | A61F 2/28 623/17.16 |
| 2004/0115172 A1 | 6/2004 | Bianchi et al. | |
| 2005/0152882 A1 | 7/2005 | Kizer et al. | |
| 2005/0251268 A1 | 11/2005 | Truncale | |
| 2006/0200235 A1 | 9/2006 | Bianchi et al. | |
| 2006/0200236 A1 | 9/2006 | Bianchi et al. | |
| 2006/0212036 A1 | 9/2006 | Bianchi et al. | |
| 2006/0229722 A1 | 10/2006 | Bianchi et al. | |

OTHER PUBLICATIONS

Ito et al., "Transplantation of tissue-engineered osteochondral plug using cultured chondrocytes and interconnected porous calcium hydroxyapatite ceramic cylindrical plugs to treat osteochondral defects in a rabbit model," Artif. Organs, 32(1):36-44 (2008).

Jiang et al., "Repair of porcine articular cartilage defect with a biphasic osteochondral composite," J. Orthop. Res., 25 (10):1277-1290 (2007).

Smith & Nephew, Trufit BGS PLUB Webpage (overview), Dec. 1, 2008, http://global.smith-nephew.com/us product23822.htm.

Smith & Nephew, Trukor Plus technique guide webpage, Jun. 3, 2008, http://global.smith-nephew.com/us/23820_23868.htm.

Smith & Nephew, Trukor Plus Webpage (overview), Jun. 3, 2008, http://global.smith-nephew.com/us/jointresurfacing/product23820.htm.

Tanaka et al., "Use of biphasic graft constructed with chondrocytes overlying a beta-tricalcium phosphate block in the treatment of rabit osteochondral defects," Tissue Eng., 11(1-2):331-339 (2005).

Von Rechenberg et al., "Mosaicplasty with Photooxidized, Mushroom Shaped, Bovine, Osteochondral Xenografts in Experimental Sheep," Vet. Comp. Orthop. Traumatol., 19(3):147-156 (2006).

Williams et al., "Articular cartilage repair using a resorbable matric scaffold," Instr. Course Lect., 57:563-571 (2008).

PCT, International Search Report, Application No. PCT/US2009/047327, dated Jul. 29, 2009, 3 pages.

PCT, Written Opinion, Application No. PCT/US2009/047327, dated Jul. 29, 2009, 6 pages.

International Preliminary Report on Patentability for International Application No. PCT/US20091047327, dated Dec. 29, 2010 with Written Opinion of the International Searching Authority, pp. 1-8.

* cited by examiner

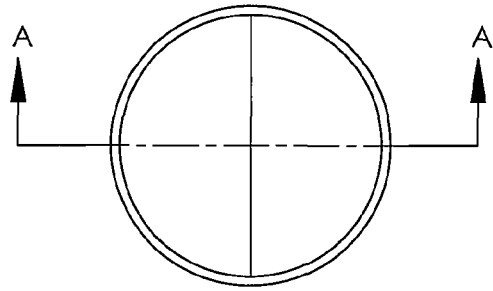
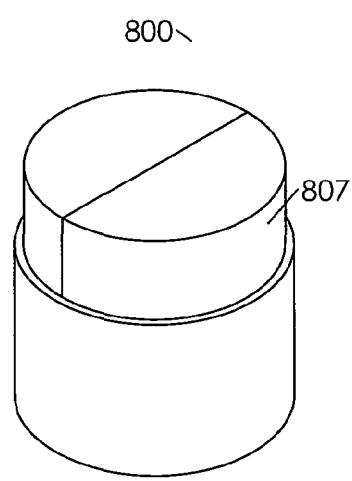
FIG. 8A
FIG. 8B
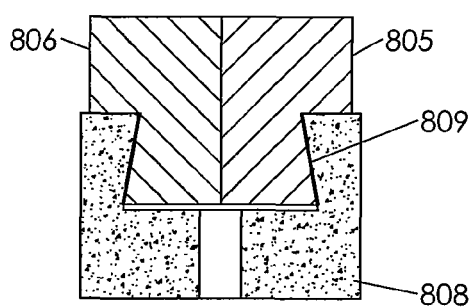
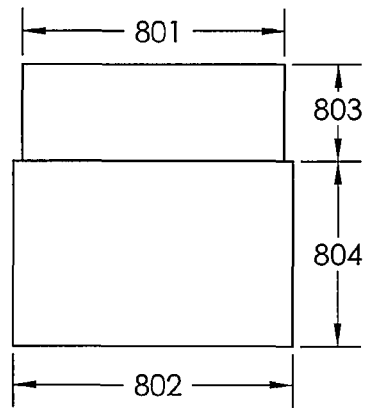
FIG. 8C
Section A-A
FIG. 8D Section A-A

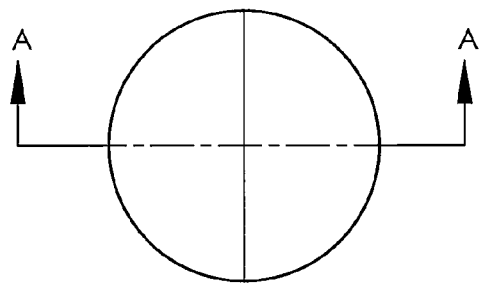
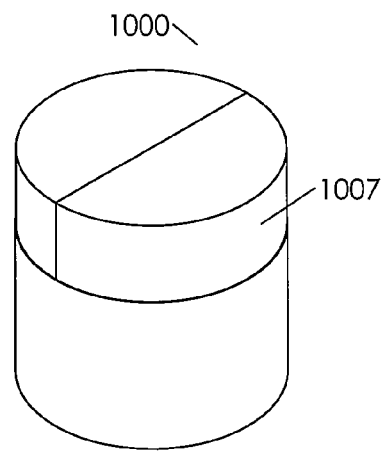
FIG. 10A
FIG. 10B
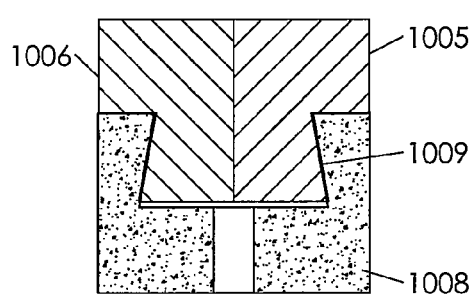
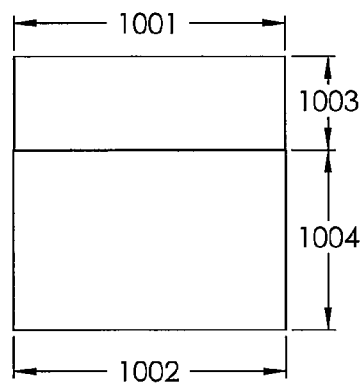
FIG. 10C
Section A-A
FIG. 10D Section A-A

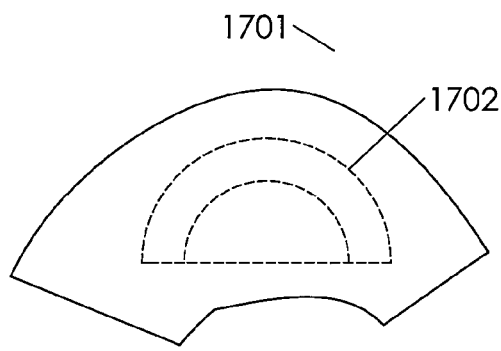
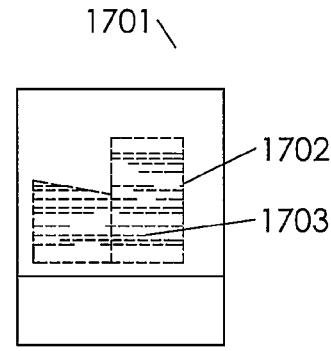
FIG. 17A  FIG. 17B
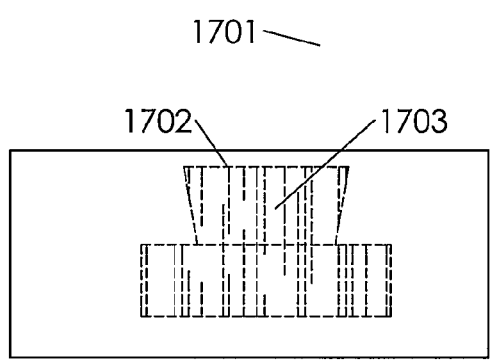
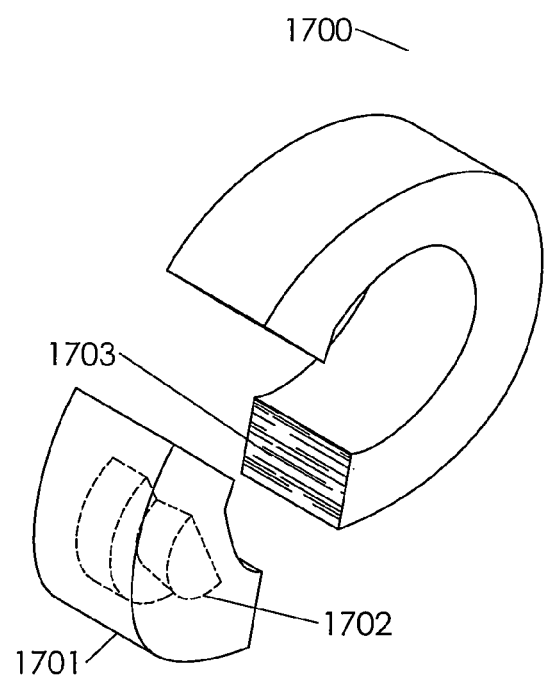
FIG. 17C  FIG. 17D

ASSEMBLED CARTILAGE REPAIR GRAFT

RELATED APPLICATIONS

This application claims priority to, and is a continuation of, U.S. patent application Ser. No. 12/140,210, having a filing date of Jun. 16, 2008, now abandoned, which is incorporated herein by reference, and which also claims priority to PCT Patent Application No. PCT/US2009/047327, having a filing date of Jun. 15, 2009, all of which are incorporated herein by reference in their entirety.

BACKGROUND OF THE INVENTION

Focal articular cartilage defects of the knee are not uncommon consequences of injuries from sports, work or activities of daily living. Arthroscopic studies have estimated the occurrence of near full thickness lesions, full thickness lesions or full thickness with boney involvement lesions greater than 1 cm$^2$ to be in the range of 6% of all surgical procedures in the knee. These types of articular cartilage defects may cause pain, swelling and/or knee locking and thus diminish the individual's overall quality of life. The size (area dimensions), depth (partial cartilage tissue to boney involvement), containment, co-morbidities (e.g., ACL tear, meniscal tear, and malalignment) and region of a defect will influence the procedure used by surgeons. Currently, for focal defects smaller than (<) 2.5 cm$^2$, the subject and surgeon have few options: debridement (chondroplasty), marrow stimulation (micro-fracture, abrasionoplasty, or subchondral drilling), or autograft osteochondral plugs (OATS, COR, mosaicoplasty). For defects greater than (>) 2.5 cm$^2$, the options are allograft osteochondral plugs or autologous cultured chondrocytes (e.g. Carticel® in the United States). While these procedures show significant rates of clinical success in the short and medium term, they each have limitations ranging from the quality of the cartilage repair to the cost and complexity of surgical procedures. Additionally, some of the procedures themselves create defects (i.e. OATS) either as a direct result of the primary procedure or through second site morbidity caused by the recovery of the patient's own tissue.

The surfaces of joints that face the joint cavity are covered with a mechanically robust connective tissue layer called chondral surface or cartilage layer. Underneath the cartilage layer is a cancellous bone termed subchondral bone. The chondral surface or cartilage layer is the primary functional surface of joints such as the knee, elbow, or shoulder. The cartilage cushions shock, carries the compressive loads placed on the joint, and allows for smooth and controlled movement between the bones in the joint. The subchondral bone supports the cartilage layer by providing blood flow, nutrients and structural integrity.

BRIEF SUMMARY OF THE INVENTION

The present invention provides assembled implants and articular cartilage repair implants particularly useful in the field of orthopedic or sports medicine surgery, and generally useful for the repair, replacement and regrowth of articulating cartilage surfaces.

In one aspect of the present invention, a bifunctional bioabsorbable assembled implant adapted for implantation at a site of a bone cartilage junction is provided. The bifunctional implant has the ability to promote growth of at least two different tissue types, such as cartilage and bone, at adjacent areas of a single implant site. The bifunctional implant preferably has an osteoconductive portion adapted to fill a defect in a subchondral bone layer, and a chondroinductive portion adapted to fill a corresponding cartilage layer. The osteoconductive portion and the chondroinductive portion are derived from the same or different source materials and preferably are assembled in a stacked relationship.

A bifunctional implant is particularly beneficial in the treatment of osteochondral defects in an articulating cartilage joint surface. An osteoconductive portion of the implant provides proper physical properties for implantation and anchoring of the implant while promoting the ingrowth and healing of the underlying subchondral bone tissue. An osteoconductive portion further provides the proper biomechanical properties to support and maintain the implant during remodeling, including sufficient porosity (or permeability), strength and stiffness approximating those of native subchondral bone. A chondroinductive portion provides the proper physical properties to support anatomical loads and maintain integrity of the joint while promoting the ingrowth and healing of native cartilaginous tissue. A chondroinductive portion further provides the proper biomechanical properties to support and maintain the implant during remodeling, including sufficient porosity (or permeability), strength and stiffness approximating those of native cartilaginous tissue.

In another aspect an assembled cartilage repair implant, suitable for implant at an osteochondral site in a human patient, and assembled via a hydration controlled interference fit is provided, including at least one osteoconductive cancellous bone portion, and at least one chondroinductive demineralized cortical bone portion. The cancellous bone portion and the cortical bone portion are preferably assembled in a stacked relationship.

In another aspect an assembled biological implant shaped and sized for implantation into a bone cartilage junction is provided, having a first region of osteoconductive cancellous bone material and a second region of chondroinductive cortical bone material, wherein the first and second regions are joined by a hydration controlled shrink fit. In some embodiments, the first region is a lower region or base, and the second region is an upper region or cap.

In another aspect of the present invention an implant adapted for implantation at an articulating cartilage site is provided, having a perforated membrane of demineralized cortical bone. The membrane defines a plane by the membrane's length and width (its longer dimensions). The membrane includes natural Haversian canals oriented in the plane of the membrane. Natural Haversian canals oriented generally parallel to or at an oblique angle to the plane of the membrane may advantageously provide transport, signaling, and growth pathways between or in addition to any added perforation, canals or other features to support ingrowth, chondroinduction and chondroconduction.

In another embodiment, the membrane is recovered from a long bone in a radial section wherein the Haversian canals are oriented transverse to the thickness of the membrane, running along either the length or width of the membrane, or both. In this alternative embodiment, holes are drilled or otherwise formed across the thickness of the membrane after demineralization to provide a chondroinductive membrane.

In another aspect of the present invention, a method of using an assembled cartilage repair implant is provided, including filling an osteochondral defect having a subchondral bone layer and a cartilaginous layer with an assembled implant adapted for implantation at a bone cartilage junction. The assembled implant includes at least one osteoconductive or synthetic portion, preferably of cancellous bone, and at least one chondroinductive portion, preferably of demineralized cortical bone, such that the subchondral bone layer of the defect is filled with the osteoconductive (or synthetic) portion, and the cartilaginous layer of the defect is filled with the chondroinductive demineralized cortical bone portion.

In another aspect a method is provided for the treatment of cartilaginous tissue in a mammal, including filling a defect site with an assembled bifunctional biological implant adapted for implantation at a bone cartilage junction, such that a first region of the defect site is filled by osteoconductive cancellous bone material and a second region of the defect site is filled by chondroinductive cortical bone material. In some embodiments, the first region is a lower region or base, and the second region is an upper region or cap.

In another aspect a method of making a bifunctional bioabsorbable assembled implant adapted for implantation at the site of a bone cartilage junction is provided, including the steps of providing an osteoconductive portion adapted to fill a defect in a subchondral bone layer, and assembling the osteoconductive portion with a chondroinductive portion adapted to fill a cartilage layer, wherein the osteoconductive portion and the chondroinductive portion are assembled via a hydration controlled interference fit.

In another aspect a method is provided for making an assembled biological implant shaped and sized for implantation into a bone cartilage junction, including the steps of providing a first region of cortical bone material in a dehydrated state, and assembling the cortical bone material with a second region of cancellous bone material, wherein the dehydrated cortical bone material is rehydrated after assembly.

In another aspect, a method of making an assembled bifunctional implant is provided, including the steps of: providing a portion of mineralized cortical bone in a hydrated state; machining the portion of mineralized cortical bone to produce a hydrated machined mineralized cortical bone portion; demineralizing the hydrated machined mineralized cortical bone portion to produce a hydrated machined demineralized cortical bone portion; dehydrating the hydrated machined demineralized cortical bone portion, to produce a dehydrated machined demineralized cortical bone portion; providing a portion of mineralized cancellous bone, which is dehydrated, partially hydrated or hydrated; assembling the dehydrated machined demineralized cortical bone portion and the mineralized cancellous bone portion, and rehydrating at least one of the bone portions assembled together, to produce a hydration controlled interference fit in the assembly. In some embodiments, at least one geometric feature of the assembly or of one of the assembled bone portions is machined to a predetermined dimension. Optionally, the hydrated machined mineralized cancellous bone portion may also be demineralized.

The present implants have been shown to produce a particularly preferred embodiment with a combination of assembled elements including a substantially cylindrical chondroinductive portion, having at least one substantially flat, smooth or rounded end surface, assembled from two pieces of chondroinductive demineralized cortical bone, alternatively assembled from three or four pieces of chondroinductive demineralized cortical bone. The pieces of demineralized cortical bone are preferably substantially similar, mirrored, or radially symmetric with respect to each other. Alternatively, a single piece of substantially cylindrical chondroinductive demineralized cortical bone, preferably having at least one substantially flat, smooth or rounded end surface, may be used effectively, especially when producing smaller size implants, wherein the chondroinductive demineralized cortical bone piece is preferably radially symmetric or symmetric about a plane passing through its center axis, or both.

The chondroinductive portion(s) of this particularly preferred embodiment are assembled together, or held in place in the case of a single piece of chondroinductive demineralized cortical bone, by a hydration controlled interference fit which is also a shrink fit and a negatively tapered shaft and bore fit, with a substantially cylindrical osteoconductive portion of mineralized cancellous bone, the cancellous portion preferably having at least one substantially flat, smooth or rounded end surface. In this embodiment, the osteoconductive piece of mineralized cancellous bone completely surrounds a part of the chondroinductive portion to capture and secure it in place.

The outer substantially cylindrical profile of the implant, formed by the union of a substantially cylindrical chondroinductive portion, preferably having at least one substantially flat, smooth or rounded end surface, assembled from two pieces of chondroinductive demineralized cortical bone together with a substantially cylindrical osteoconductive piece of mineralized cancellous bone, preferably having at least one substantially flat, smooth or rounded end surface, provides an implant adapted for insertion with widely used arthroscopic surgical technique, instrumentation and fixation.

A further advantage of this embodiment, especially when an assembled chondroinductive portion is used, is that the negatively tapered shaft and bore fit provides solid and secure assembly wherein the at least two pieces of chondroinductive demineralized cortical bone are in direct contact with each other and are completely or partially surrounded over at least a part of their surface at the hydration controlled interference fit interface by a piece of osteoconductive cancellous bone.

An advantage of the assembly methods, and especially of the hydration controlled interference fit or hydration controlled shrink fit, is that the assembled implants are suitable for implantation at an osteochondral site in a human or other mammal without additional internal fasteners or connective elements such as press fit pins, bone pins, sutures, or adhesives. In addition to requiring excess material and additional processing steps, these other fasteners or connective elements add extra cost and complications to the design, manufacture and use of the implants. A preferred embodiment of the present invention provides an assembly that does not comprise separate fasteners or adhesive for holding together the implant.

Alternatively, certain embodiments of the present implants provide an assembly including additional internal fasteners or connective elements such as press fit pins, bone pins, sutures, or adhesives. These additional external fasteners may be employed either in conjunction with or in place of a hydration controlled interference fit to provide additional strength or reinforcement, or to provide additional elements such as growth factors, cells or specific scaffold materials to promote healing, chondroinduction, osteoinduction or osteoconduction.

BRIEF DESCRIPTION OF SEVERAL VIEWS OF THE DRAWINGS

FIGS. 8A-8D show top, perspective, section and side views, respectively, of an assembled implant wherein the chondroinductive cap is smaller than the osteoconductive base.

FIGS. 10A-10D show top, perspective, section and side views, respectively, of an assembled implant wherein the chondroinductive cap is substantially or about the same size as the osteoconductive base.

FIGS. 17A-17C show a series of orthogonal views of the shaft of a long bone, wherein the cortical bone source material is recovered, advantageously producing an implant having naturally occurring internal canals. FIG. 17D shows an exploded perspective view of a hemi cylindrical cortical bone portion blank cut from a section of the shaft of a long bone.

DETAILED DESCRIPTION OF THE INVENTION

Figure 1A:
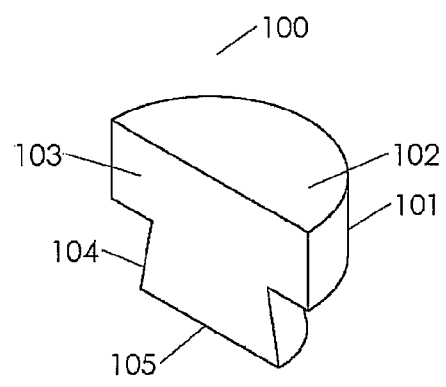
FIGS. 1A-1D show perspective views of each of four different steps in the process of making one embodiment of the present implants.

The present invention provides bifunctional implants useful in the replacement and repair of damaged cartilaginous or articular cartilage tissue. The invention also provides assembled implants comprising a chondroinductive portion and an osteoconductive portion assembled to form a bifunctional implant. The invention further provides assembled implants having a top portion or cap of chondroinductive demineralized cortical bone assembled in a hydration controlled interference fit with a bottom portion or base of osteoconductive mineralized cancellous bone to form a bifunctional implant matched to the anatomy of an osteoarticular surgical site and suited to the arthroscopic repair of osteoarticular defects.

The present disclosure describes bifunctional implants suitable for non load bearing and lower wear application such as the backfill of autograft core harvest sites where the autograft tissue is used as the implant plug in the primary damage repair site (e.g. OATS procedure). The present disclosure further describes bifunctional implants suitable for load bearing and high wear applications such as direct implantation in the primary surgically created defect replacing a section of diseased cartilaginous or osteochondral tissue.

As one of the preferred embodiments, a cylindrical bifunctional biological assembled implant is provided which is adapted for implantation at the site of a bone cartilage junction, with an osteoconductive mineralized cancellous allograft bone portion adapted to fill a defect in a subchondral bone layer assembled in a stacked relationship with a chondroinductive demineralized cortical allograft bone portion adapted to fill a corresponding cartilage layer. Cylindrical implants are preferred for their ease of use and compatibility with known surgical methods and instruments.

Current instrument sets utilize hollow cylindrical coring bits, drills or punches to make circular or cylindrical cuts and defects at the osteochondral site. These cylindrical instruments produce generally cylindrical autograft plugs and generally cylindrical osteochondral defects or surgically created defects. Instrumentation designed for recovery, transport, handling and implantation of osteochondral implants also makes use of hollow cylindrical geometry to manage these implants, cores, or transplants. Therefore, the manufacture of cylindrical implants is highly preferred not only for its rotational symmetry, ease of manufacture and absence of stress concentrations, but also for its ease of implantation and compatibility with currently available instrumentation sets.

Although cylindrical implant configurations are used extensively to exemplify embodiments of the present implants throughout the specification and figures, it is contemplated that the implants and methods of the present invention are operable with other implant configurations, including polygonal, square, rectangular, triangular, substantially cylindrical, substantially square, substantially triangular, substantially rectangular, rectilinear, curvilinear, arcuate, non-arcuate, and irregular implant body shapes.

In some embodiments, the present implants provide a concave, convex, irregular or complexly curved upper surface, adapted to approximate the surface geometry of an articulating cartilage site, advantageously reducing peak forces on the implant during rehabilitation and remodeling following surgery. In other embodiments the implants advantageously provide concave, convex, arcuate, non-arcuate, planar, non-planar or irregular surfaces at the interface between two portions or between two pieces in the assembly or at the external interface between the implant and the surgical site. These shapes are advantageously employed to enhance placement, orientation or fixation of the implant or between elements of the assembly.

The chondroinductive portion is preferably sized to substantially approximate the depth of the cartilage layer at a site of implantation. The osteoconductive portion is preferably sized to at least about 1.5 times the depth of the chondroinductive portion, to allow a solid fixation at the surgical site and to prevent dislodgement of the implant following surgery.

The osteoconductive portions and chondroinductive portions each define a characteristic depth and a characteristic width or characteristic diameter. In one embodiment, the characteristic depth of the osteoconductive portion is substantially equivalent to or greater than the characteristic depth of the chondroinductive portion. In another embodiment, the characteristic depth of the osteoconductive portion is at least about one and one half times greater than the characteristic depth of the chondroinductive portion, and the characteristic width of the osteoconductive portion is greater than the characteristic width of the chondroinductive portion. Various other ratios of width and depth are contemplated, as well as alternative configurations including more than two portions.

An interference fit exists when two or more parts are assembled together with interference in the mating dimension or dimensions, such that two or more parts attempt to occupy the same space. The stress created as one or more of the parts attempts to occupy the same space with the other results in forces which generally act to hold the assembly together. Interference fits are generally accomplished either by forcing or pressing the interfering parts together in a press fit, or by creating a condition, typically by heating and cooling and/or by adding or removing moisture, where the parts are without interference during the assembly process and then shrink or swell to a create an interference fit. Shrinkage and swelling of a chondroinductive portion may be a variable phenomenon across a given geometry, sometimes resulting in warping or deformation of a dehydrated part. Upon rehydration, however, most materials will return substantially to their original shape. An interference fit, press fit or shrink fit may include a straight or tapered shaft and bore fit.

The pieces assembled together may include an osteoconductive portion and a chondroinductive demineralized cortical bone portion having a series of canals. The canals may be manufactured or naturally occurring in the bone material, and may be oriented in a direction communicating between the osteoconductive portion and at least one surface of the chondroinductive demineralized cortical bone portion. The canals are preferably oriented in alignment with or substantially parallel to a major axis of the interference fit, press fit, or shrink fit. For example, the canals may be oriented such that they travel in a direction along the axis of the cylinder or bore in a bore and cylinder interference fit. In a preferred embodiment, naturally occurring Haversian canals of the cortical bone material are in substantial alignment with a major body axis of the implant, and/or in communication with one or more end surfaces of the implant. Alternatively, the canals, or a majority or substantial percentage of the canals, may be oriented at an angle to or perpendicular to a major axis of the interference fit, press fit, or shrink fit.

The implants of the present invention may have a graft manipulation hole, which is advantageous for aiding graft placement and may also serve as an additional conduit or channel allowing access of blood and other fluids from the surgical implantation site into the implant interior (in addition to any natural or artificial canals present in the implant). Such holes are preferably in the base portion of an assembled implant or in the central or edge areas of a membrane implant. When the implant is a membrane type implant, the hole is preferably pre-machined, formed or punched and may be used for fixation of the implant. The implant may have one or more of these fixation holes, depending on configuration. Fixation devices for use in these holes may be, but are not limited to, suture, pins, staples, and bone pins When the implant is an assembled implant having a cap and a base portion, if the base material is porous, such as cancellous bone material, the hole is optional and may be replaced by a flat bottom in the base portion, providing additional strength and structural integrity.

The Figures, and the discussion thereof, provided in this disclosure relate to various embodiments of the present technology. It should be understood that the Figures are illustrative in nature, and that modifications can be made thereto without departing from the scope of the present invention.

FIGS. 1A-1D show perspective views of each of four different steps in the process of making one embodiment of the present implants.

FIG. 1A shows a perspective view of one fully hydrated piece 100 of a portion suitable for assembly in an implant having a cylindrical profile 101, flat top portion 102, a flat mating surface 103, a negatively tapered shaft 104, and a flat bottom surface 105. Features 101 to 105 are shown in the fully hydrated or as machined state in FIG. 1A. The piece 100 may be assembled with another piece of the same or of different design to form a chondroinductive portion, and is preferably machined from cortical bone, then demineralized.

Figure 1B:
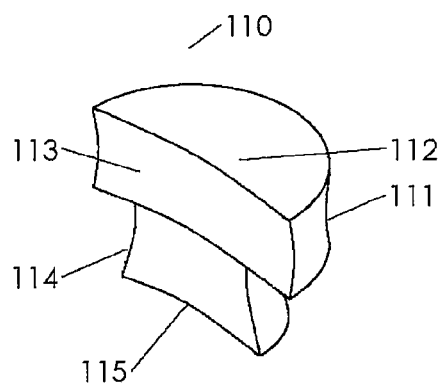

FIG. 1B shows a perspective view of one dehydrated piece 110 of a portion suitable for assembly in an implant having a shrunken but still substantially cylindrical profile 111, a shrunken but still substantially flat top portion 112, a shrunken and withdrawn flat mating surface 113, a shrunken negatively tapered shaft 114, and a shrunken but still substantially flat bottom surface 115. Features 111 to 115 are shown in the dehydrated or shrunken state in FIG. 1B. The piece 110 may be assembled with another piece of the same or of different design to form a chondroinductive portion, and is preferably machined from cortical bone, then demineralized.

Figure 1C:
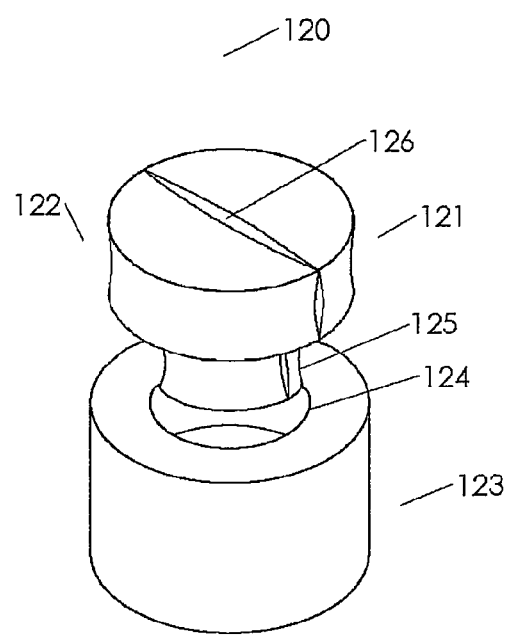

FIG. 1C shows a perspective view of an exploded or in process view of a 3 piece assembly 120. Pieces 121 and 122 are dehydrated pieces, preferably chondroinductive and preferably of demineralized cortical bone, aligned in position for assembly with a third piece 123. Piece 123 is a base portion, preferably osteoconductive and preferably of mineralized cancellous bone, aligned in position for assembly with pieces 121 and 122. Piece 123 has a bore 124 which is of substantially equivalent diameter or slightly larger than shaft 125 formed by the two pieces 121 and 122 in their dehydrated state. A gap 126 is visible between the mating faces of dehydrated piece 121 and dehydrated piece 122.

Figure 1D:
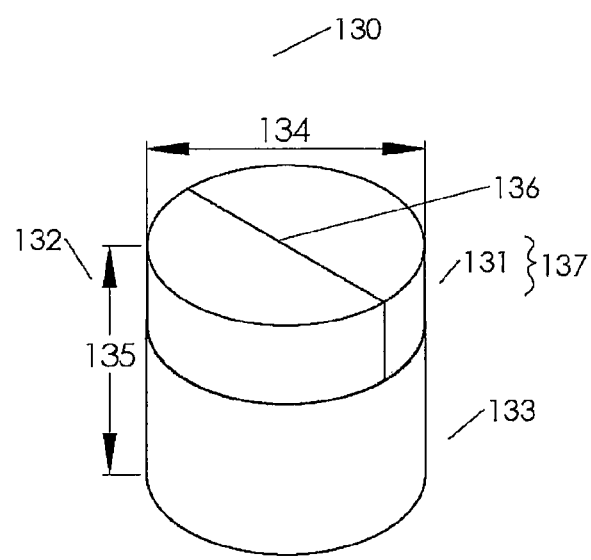

FIG. 1D shows a perspective view of a fully hydrated complete assembly of a bifunctional implant 130. Pieces 131 and 132 are assembled to form a top or cap portion with base portion 133. The mating features (not shown) are preferably a negatively tapered shaft and bore, hydration controlled shrink fit. The implant has a characteristic width or diameter 134 and a characteristic depth, thickness or height 135. The mating faces of each of piece 131 and 132, respectively, meet to form a substantially flat interface 136 between the two pieces 131 and 132 which together make up the cap portion 137.

Figure 2:
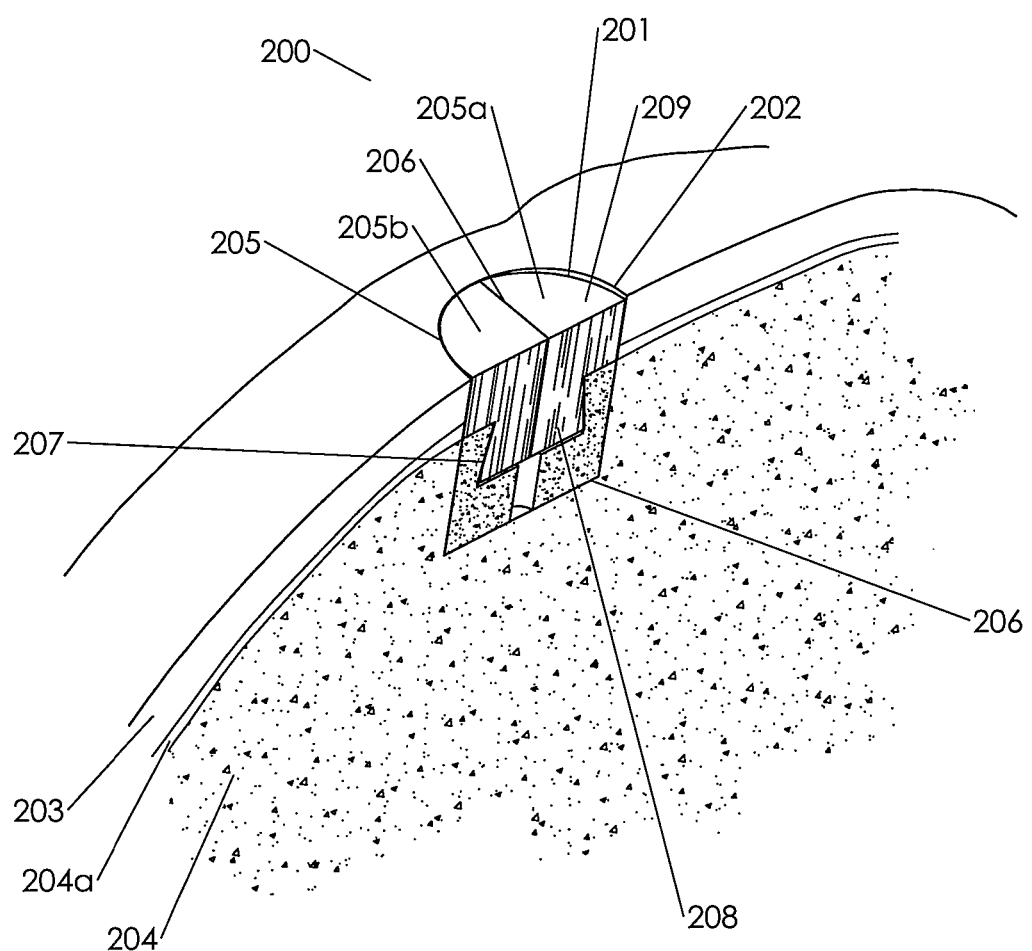
FIG. 2 shows a perspective cross sectional view of an implant implanted at an osteochondral surgical site by the present methods.

FIG. 2 shows a perspective cross sectional view of a cylindrical cartilage repair implant 201 implanted at an osteochondral surgical site 200 by the present methods. A surgically created defect 202 passes through a cartilage layer 203, through a narrow cortical bone shell layer 204a and into a subchondral bone layer 204 of the patient. A chondroinductive demineralized cortical bone cap portion 205 fills the top region of the surgical defect 202 within the cartilage layer 203. An osteoconductive cancellous bone base portion 206 fills the bottom region of the surgical defect 202 within the subchondral bone layer 204. Cap portion 205 is assembled from two pieces 205a and 205b, which meet at seam 206, visible along the top of implant 201 and through the cross section. A negatively tapered shaft and bore interference fit holds pieces 205a and 205b together with base 206. Natural Haversian canals 208 are substantially in alignment with the major axis of implant 201 and in communication between base portion 206 and top surface 209 of cap portion 205 as well as with the subchondral bone layer 204 of the patient.

FIGS. 3A-3D show a series of cross sectional views of a negatively tapered hydration controlled interference fit assembled implant. The cross sectional views of FIGS. 3A-3D preferably represent cross sections of a cylindrical implant; but may alternatively represent extruded or mirrored sections producing rectilinear, slotted, triangular, square or polygonal implants; or projected, swept or variable sections producing implants of irregular or varying cross section.

Figure 3A:
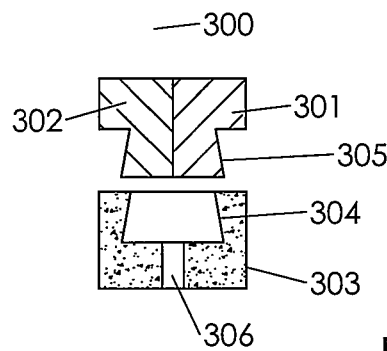
FIGS. 3A-3D show a series of cross sectional views of a negatively tapered hydration controlled interference fit assembled implant, including (A) a chondroinductive portion and an osteoconductive portion; (B) a dehydrated chondroinductive portion in position for assembly just above an osteoconductive portion; (C) an assembly of a dehydrated chondroinductive portion mated with an osteoconductive portion; and (D) a fully hydrated interference fit between a hydrated chondroinductive portion and a hydrated osteoconductive portion.
Figure 3A:
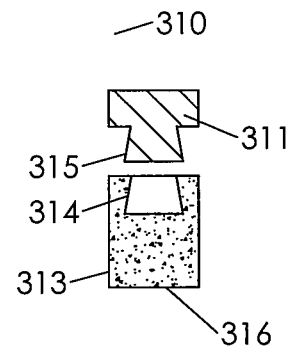

FIG. 3A shows side by side cross sectional views of two implant embodiments, one with assembled cap pieces 301 and 302 mating with base portion 303 to form a three piece assembly 300, and the other with a mono cap portion 311 mating with base portion 313 to form a two piece assembly 310. Bore 304 and bore 314 are adapted to mate with shaft 305 and shaft 315, respectively. An optional hole 306 is provided as an advantageous graft manipulation hole and as an additional conduit or channel allowing access of blood and other fluids from the surgical implantation site into the implant interior. When the base material is porous, such as cancellous bone material, the optional hole 306 may be replaced by a flat bottom 316 in the base portion 313, providing additional strength and structural integrity.

Figure 3B:
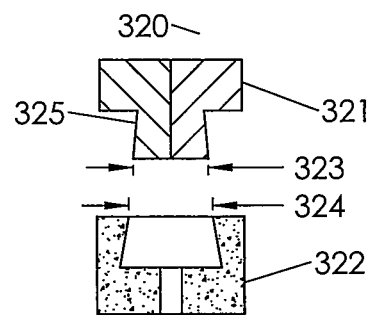
Figure 3B:
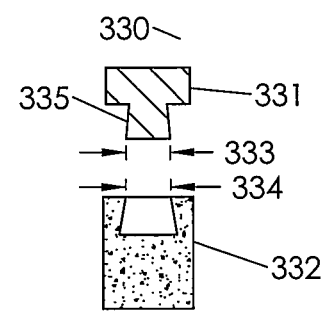

FIG. 3B shows side by side cross sectional views of two implant embodiments 320 and 330, with dehydrated chondroinductive portions 321 and 331 in position for assembly just above osteoconductive portions 322 and 332, respectively. Dehydrated chondroinductive portions 321 and 331 exhibit reduced diameter dimensions including shaft dimensions 323 and 333, respectively, which are smaller than or substantially equal to bore dimensions 324 and 334, respectively. For clarity and ease of understanding, other shrinkage and warping effects such as the drawing in, curling, warping or curving of shafts 325 and 335, respectively, are not shown.

Figure 3C:
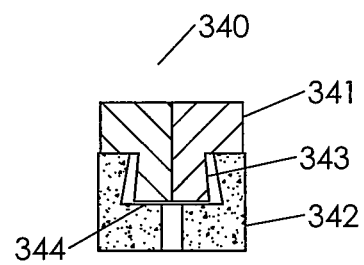
Figure 3C:
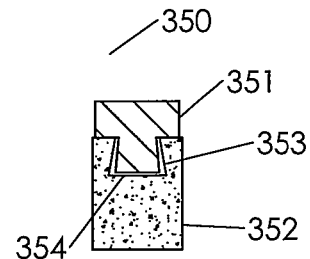

FIG. 3C shows side by side cross sectional views of two implant embodiments 340 and 350, with an assembly of dehydrated chondroinductive cap portions 341 and 351 mated with osteoconductive base portions 342 and 352, respectively. Dehydrated assembly clearance gaps 343 and 353, respectively, are visible around the shaft and bore fits of the two implant embodiments. Optional bottom clearance gaps 344 and 354, respectively, are visible in the assemblies, advantageously providing additional clearance to allow for manufacturing and assembly tolerances and providing a further interior path for infiltration, flow and transport of blood and fluids within the implant. Optionally, bottom clearance gaps 344 and 354 may be eliminated or made to an interference fit condition to maximize structural integrity and surface to surface contact within the graft interior.

Figure 3D:
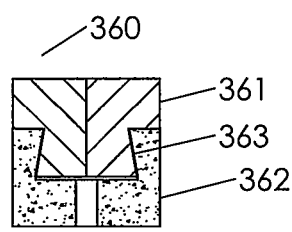
Figure 3D:
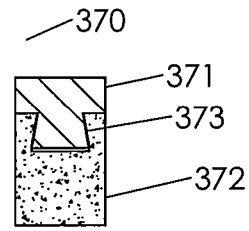

FIG. 3D shows side by side cross sectional views of two implant embodiments 360 and 370, with fully hydrated interference fits 363 and 373, between hydrated chondroinductive portions 361 and 371 and osteoconductive portions 362 and 372, respectively.

FIGS. 4A-4D show a series of cross sectional views of a positively tapered hydration controlled interference fit assembled implant. The cross sectional views of FIGS. 4A-4D preferably represent cross sections of a cylindrical implant; but may alternatively represent extruded or mirrored sections producing rectilinear, slotted, triangular, square or polygonal implants; or projected, swept or variable sections producing implants of irregular or varying cross section.

Figure 4A:
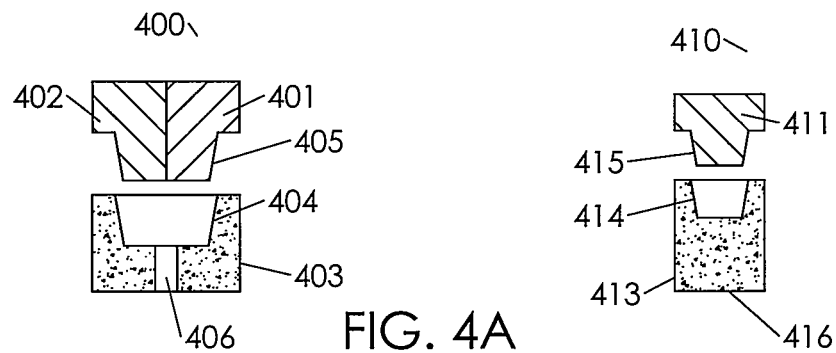
FIGS. 4A-4D show a series of cross sectional views of a positively tapered hydration controlled interference fit assembled implant, including (A) a chondroinductive portion and an osteoconductive portion; (B) a dehydrated chondroinductive portion in position for assembly just above an osteoconductive portion; (C) an assembly of a dehydrated chondroinductive portion mated with an osteoconductive portion; and (D) a fully hydrated interference fit between a hydrated chondroinductive portion and a hydrated osteoconductive portion.
Figure 4A:
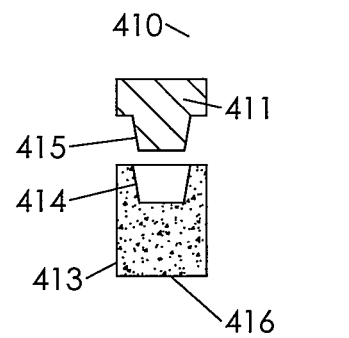

FIG. 4A shows side by side cross sectional views of two implant embodiments, one with assembled cap pieces 401 and 402 mating with base portion 403 to form a three piece assembly 400, and the other with a mono cap portion 411 mating with base portion 413 to form a two piece assembly 410. Bore 404 and bore 414 are adapted to mate with shaft 405 and shaft 415, respectively. An optional hole 406 is provided as an advantageous graft manipulation hole and as an additional conduit or channel allowing access of blood and other fluids from the surgical implantation site into the implant interior. When the base material is porous, such as cancellous bone material, the optional hole 406 may be replaced by a flat bottom 416 in the base portion 413, providing additional strength and structural integrity.

Figure 4B:
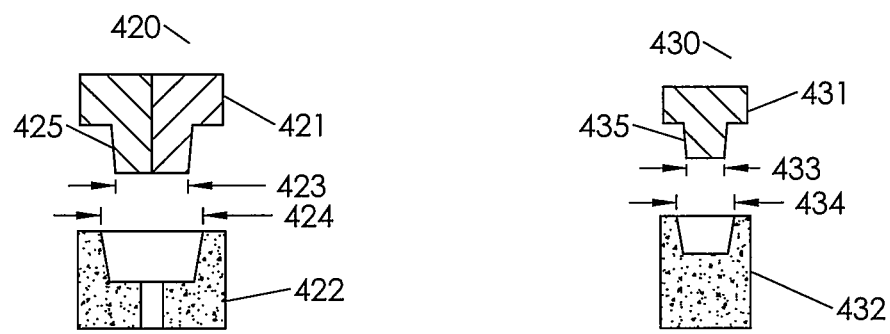
Figure 4B:
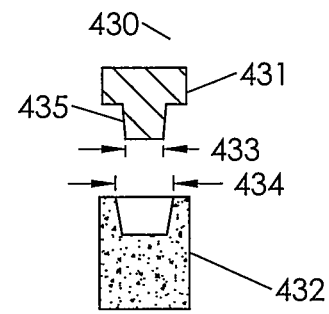

FIG. 4B shows side by side cross sectional views of two implant embodiments 420 and 430, with dehydrated chondroinductive portions 421 and 431 in position for assembly just above osteoconductive portions 422 and 432, respectively. Dehydrated chondroinductive portions 421 and 431 exhibit reduced diameter dimensions including shaft dimensions 423 and 433, respectively, which are smaller than or substantially equal to bore dimensions 424 and 434, respectively. For clarity and ease of understanding, other shrinkage and warping effects such as the drawing in, curling, warping or curving of shafts 425 and 435, respectively, are not shown.

Figure 4C:
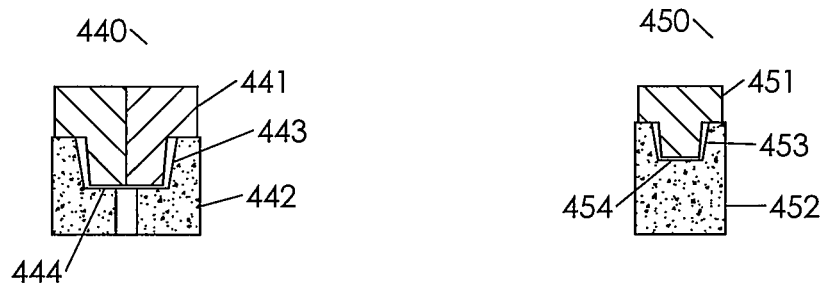
Figure 4C:
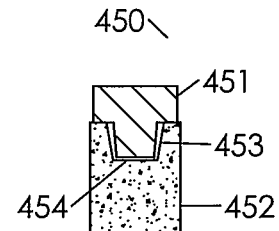

FIG. 4C shows side by side cross sectional views of two implant embodiments 440 and 450, with an assembly of dehydrated chondroinductive cap portions 441 and 451 mated with osteoconductive base portions 442 and 452, respectively. Dehydrated assembly clearance gaps 443 and 453, respectively, are visible around the shaft and bore fits of the two implant embodiments. Optional bottom clearance gaps 444 and 454, respectively, are visible in the assemblies, advantageously providing additional clearance to allow for manufacturing and assembly tolerances and providing a further interior path for infiltration, flow and transport of blood and fluids within the implant. Optionally, bottom clearance gaps 444 and 454 may be eliminated or made to an interference fit condition to maximize structural integrity and surface to surface contact within the graft interior.

Figure 4D:
Figure 4D:
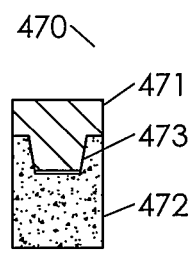

FIG. 4D shows side by side cross sectional views of two implant embodiments 460 and 470, with fully hydrated interference fits 463 and 473, between hydrated chondroinductive portions 461 and 471 and osteoconductive portions 462 and 472, respectively.

FIGS. 5A-5D show a series of cross sectional views of a non tapered hydration controlled interference fit assembled implant. The cross sectional views of FIGS. 5A-5D preferably represent cross sections of a cylindrical implant; but may alternatively represent extruded or mirrored sections producing rectilinear, slotted, triangular, square or polygonal implants; or projected, swept or variable sections producing implants of irregular or varying cross section.

Figure 5A:
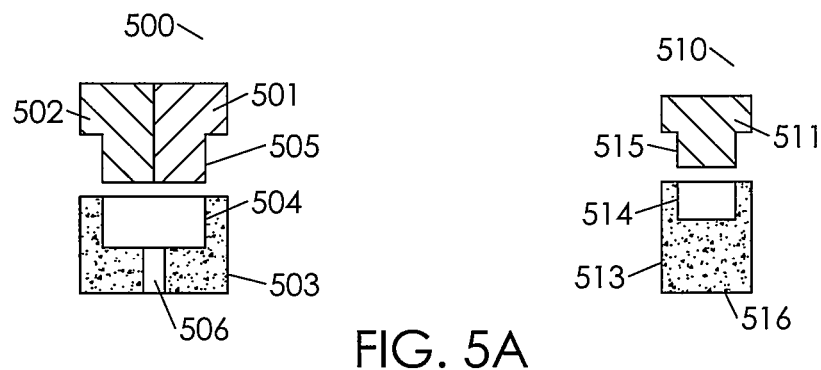
FIGS. 5A-5D show a series of cross sectional views of a non tapered hydration controlled interference fit assembled implant, including (A) a chondroinductive portion and an osteoconductive portion; (B) a dehydrated chondroinductive portion in position for assembly just above an osteoconductive portion; (C) an assembly of a dehydrated chondroinductive portion mated with an osteoconductive portion; and (D) a fully hydrated interference fit between a hydrated chondroinductive portion and a hydrated osteoconductive portion.

FIG. 5A shows side by side cross sectional views of two implant embodiments, one with assembled cap pieces 501 and 502 mating with base portion 503 to form a three piece assembly 500, and the other with a mono cap portion 511 mating with base portion 513 to form a two piece assembly 510. Bore 504 and bore 514 are adapted to mate with shaft 505 and shaft 515, respectively. An optional hole 506 is provided as an advantageous graft manipulation hole and as an additional conduit or channel allowing access of blood and other fluids from the surgical implantation site into the implant interior. When the base material is porous, such as cancellous bone material, the optional hole 506 may be replaced by a flat bottom 516 in the base portion 513, providing additional strength and structural integrity.

Figure 5B:
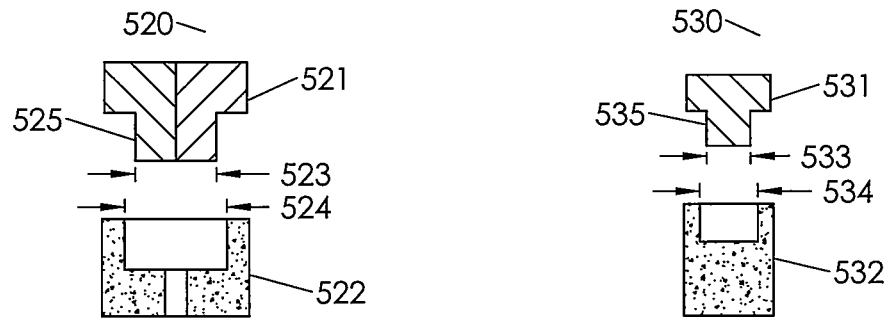

FIG. 5B shows side by side cross sectional views of two implant embodiments 520 and 530, with dehydrated chondroinductive portions 521 and 531 in position for assembly just above osteoconductive portions 522 and 532, respectively. Dehydrated chondroinductive portions 521 and 531 exhibit reduced diameter dimensions including shaft dimensions 523 and 533, respectively, which are smaller than or substantially equal to bore dimensions 524 and 534, respectively. For clarity and ease of understanding, other shrinkage and warping effects such as the drawing in, curling, warping or curving of shafts 525 and 535, respectively, are not shown.

Figure 5C:

FIG. 5C shows side by side cross sectional views of two implant embodiments 540 and 550, with an assembly of dehydrated chondroinductive cap portions 541 and 551 mated with osteoconductive base portions 542 and 552, respectively. Dehydrated assembly clearance gaps 543 and 553, respectively, are visible around the shaft and bore fits of the two implant embodiments. Optional bottom clearance gaps 544 and 554, respectively, are visible in the assemblies, advantageously providing additional clearance to allow for manufacturing and assembly tolerances and providing a further interior path for infiltration, flow and transport of blood and fluids within the implant. Optionally, bottom clearance gaps 544 and 554 may be eliminated or made to an interference fit condition to maximize structural integrity and surface to surface contact within the graft interior.

Figure 5D:

FIG. 5D shows side by side cross sectional views of two implant embodiments 560 and 570, with fully hydrated interference fits 563 and 573, between hydrated chondroinductive portions 561 and 571 and osteoconductive portions 562 and 572, respectively.

FIGS. 6A-6D show a series of cross sectional views of a non tapered undercut step or counter bore hydration controlled interference fit assembled implant. The cross sectional views of FIGS. 6A-6D preferably represent cross sections of a cylindrical implant; but may alternatively represent extruded or mirrored sections producing rectilinear, slotted, triangular, square or polygonal implants; or projected, swept or variable sections producing implants of irregular or varying cross section.

Figure 6A:
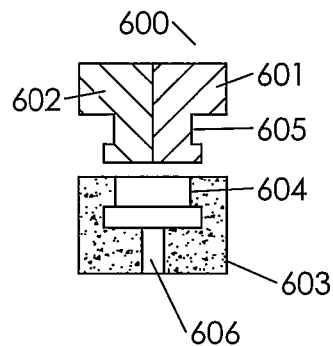
FIGS. 6A-6D show a series of cross sectional views of a non tapered undercut step or counter bore hydration controlled interference fit assembled implant, including (A) a chondroinductive portion and an osteoconductive portion; (B) a dehydrated chondroinductive portion in position for assembly just above an osteoconductive portion; (C) an assembly of a dehydrated chondroinductive portion mated with an osteoconductive portion; and (D) a fully hydrated interference fit between a hydrated chondroinductive portion and a hydrated osteoconductive portion.
Figure 6A:
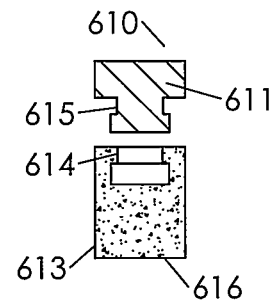

FIG. 6A shows side by side cross sectional views of two implant embodiments, one with assembled cap pieces 601 and 602 mating with base portion 603 to form a three piece assembly 600, and the other with a mono cap portion 611 mating with base portion 613 to form a two piece assembly 610. Stepped bore 604 and stepped bore 614 are adapted to mate with stepped shaft 605 and stepped shaft 615, respectively. An optional hole 606 is provided as an advantageous graft manipulation hole and as an additional conduit or channel allowing access of blood and other fluids from the surgical implantation site into the implant interior. When the base material is porous, such as cancellous bone material, the optional hole 606 may be replaced by a flat bottom 616 in the base portion 613, providing additional strength and structural integrity.

Figure 6B:
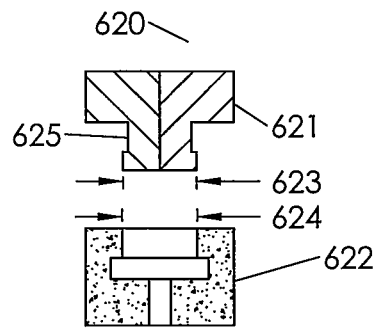
Figure 6B:
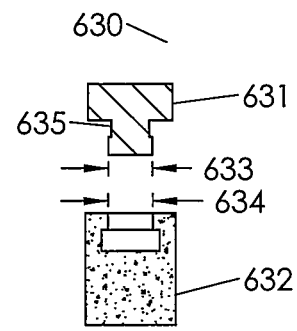

FIG. 6B shows side by side cross sectional views of two implant embodiments 620 and 630, with dehydrated chondroinductive portions 621 and 631 in position for assembly just above osteoconductive portions 622 and 632, respectively. Dehydrated chondroinductive portions 621 and 631 exhibit reduced diameter dimensions including shaft dimensions 623 and 633, respectively, which are smaller than or substantially equal to bore dimensions 624 and 634, respectively. For clarity and ease of understanding, other shrinkage and warping effects such as the drawing in, curling, warping or curving of shafts 625 and 635, respectively, are not shown.

Figure 6C:
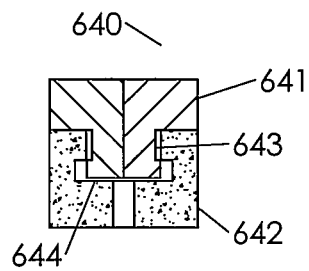
Figure 6C:
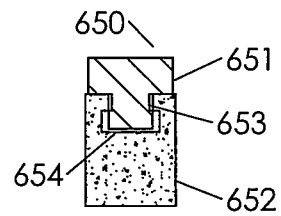

FIG. 6C shows side by side cross sectional views of two implant embodiments 640 and 650, with an assembly of dehydrated chondroinductive cap portions 641 and 651 mated with osteoconductive base portions 642 and 652, respectively. Dehydrated assembly clearance gaps 643 and 653, respectively, are visible around the shaft and bore fits of the two implant embodiments. Optional bottom clearance gaps 644 and 654, respectively, are visible in the assemblies, advantageously providing additional clearance to allow for manufacturing and assembly tolerances and providing a further interior path for infiltration, flow and transport of blood and fluids within the implant. Optionally, bottom clearance gaps 644 and 654 may be eliminated or made to an interference fit condition to maximize structural integrity and bone to bone contact within the graft interior.

Figure 6D:
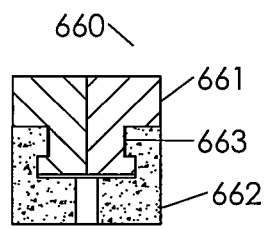
Figure 6D:
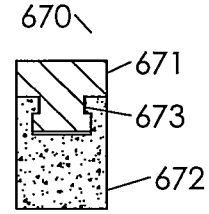

FIG. 6D shows side by side cross sectional views of two implant embodiments 660 and 670, with fully hydrated interference fits 663 and 673, between hydrated chondroinductive portions 661 and 671 and osteoconductive portions 662 and 672, respectively.

Figure 7A:
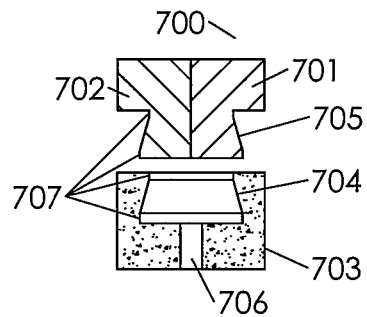
FIGS. 7A-7D show a series of cross sectional views of a negatively tapered hydration controlled interference fit assembled implant, including (A) a chondroinductive portion and an osteoconductive portion; (B) a dehydrated chondroinductive portion in position for assembly just above an osteoconductive portion; (C) an assembly of a dehydrated chondroinductive portion mated with an osteoconductive portion; and (D) a fully hydrated interference fit between a hydrated chondroinductive portion and a hydrated osteoconductive portion.
Figure 7A:
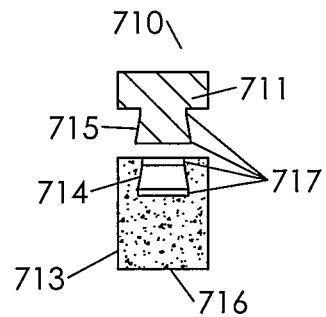

FIGS. 7A-7D show a series of cross sectional views of a negatively tapered stepped bore hydration controlled interference fit assembled implant. The cross sectional views of FIGS. 7A-7D preferably represent cross sections of a cylindrical implant; but may alternatively represent extruded or mirrored sections producing rectilinear, slotted, triangular, square or polygonal implants; or projected, swept or variable sections producing implants of irregular or varying cross section FIG. 7A shows side by side cross sectional views of two implant embodiments, one with assembled cap pieces 701 and 702 mating with base portion 703 to form a three piece assembly 700, and the other with a mono cap portion 711 mating with base portion 713 to form a two piece assembly 710. Negatively tapered dual truncated bore 704 and negatively tapered dual truncated bore 714 are adapted to mate with negatively tapered dual truncated shaft 705 and negatively tapered dual truncated shaft 715, respectively. Each of negatively tapered shaft 705, negatively tapered shaft 715, negatively tapered bore 704 and negatively tapered bore 714 is truncated top and bottom, preferably by a vertical chamfer 707 as shown, alternatively by a round, angled chamfer or other geometric feature (not shown), to improve manufacturability, increase manufacturing tolerances and increase physical robustness and breakage resistance of the implant, thus forming a negatively tapered dual truncated hydration controlled interference fit implant. Truncations may be adapted to a positively tapered or non-tapered shaft and bore fit as well (not shown) and a single truncation may provide some of the benefits of a dual truncation. An optional hole 706 is provided as an advantageous graft manipulation hole and as an additional conduit or channel allowing access of blood and other fluids from the surgical implantation site into the implant interior. When the base material is porous, such as cancellous bone material, the optional hole 706 may be replaced by a flat bottom 716 in the base portion 713, providing additional strength and structural integrity.

Figure 7B:
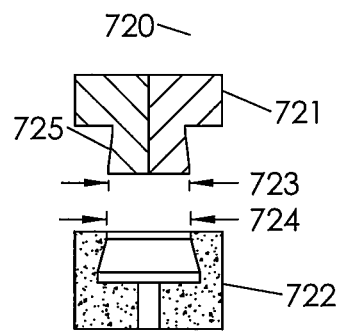
Figure 7B:
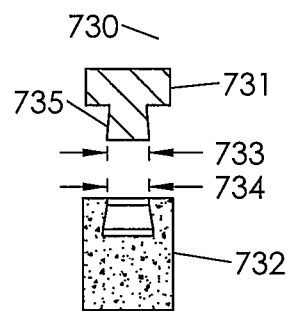

FIG. 7B shows side by side cross sectional views of two implant embodiments 720 and 730, with dehydrated chondroinductive portions 721 and 731 in position for assembly just above osteoconductive portions 722 and 732, respectively. Dehydrated chondroinductive portions 721 and 731 exhibit reduced diameter dimensions including shaft dimensions 723 and 733, respectively, which are smaller than or substantially equal to bore dimensions 724 and 734, respectively. For clarity and ease of understanding, other shrinkage and warping effects such as the drawing in, curling, warping or curving of shafts 725 and 735, respectively, are not shown.

Figure 7C:
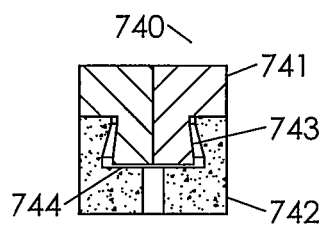
Figure 7C:
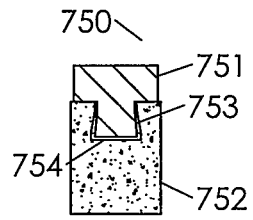

FIG. 7C shows side by side cross sectional views of two implant embodiments 740 and 750, with an assembly of dehydrated chondroinductive cap portions 741 and 751 mated with osteoconductive base portions 742 and 752, respectively. Dehydrated assembly clearance gaps 743 and 753, respectively, are visible around the shaft and bore fits of the two implant embodiments. Optional bottom clearance gaps 744 and 754, respectively, are visible in the assemblies, advantageously providing additional clearance to allow for manufacturing and assembly tolerances and providing a further interior path for infiltration, flow and transport of blood and fluids within the implant. Optionally, bottom clearance gaps 744 and 754 may be eliminated or made to an interference fit condition to maximize structural integrity and surface to surface contact within the graft interior.

Figure 7D:
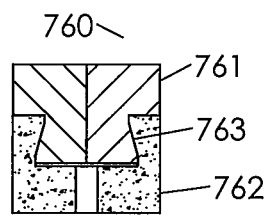
Figure 7D:
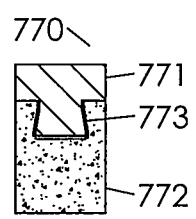
Figure 9A:
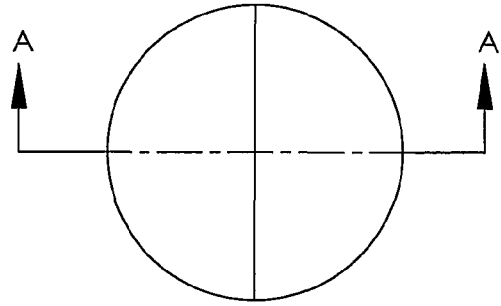
FIGS. 9A-9D show top, perspective, section and side views, respectively, of an assembled implant wherein the chondroinductive cap is larger than the osteoconductive base.
Figure 9B:
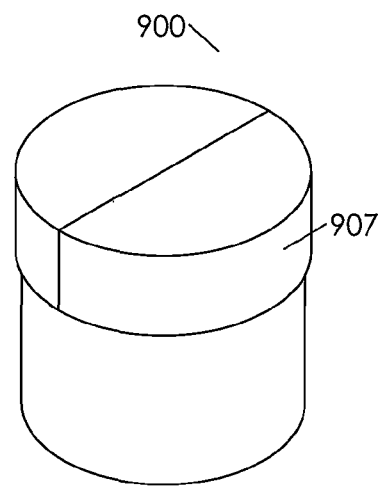
Figure 9C:
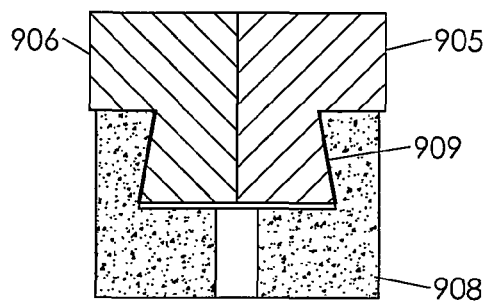
Figure 9D:
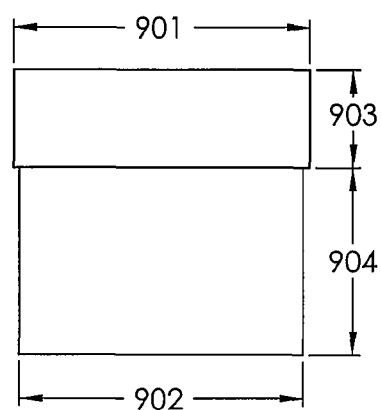

FIG. 7D shows side by side cross sectional views of two implant embodiments 760 and 770, with fully hydrated interference fits 763 and 773, between hydrated chondroinductive portions 761 and 771 and osteoconductive portions 762 and 772, respectively.

FIGS. 8A-8D show top, perspective, section and side views, respectively, of an assembled implant 800. The chondroinductive cap diameter 801 is smaller than the osteoconductive base diameter 802. The osteoconductive base height 804 is about one and one half times larger than the chondroinductive cap height 803. Assembled cap pieces 805 and 806 make up cap portion 807 which mates with base portion 808 via interference fit 809.

FIGS. 9A-9D show top, perspective, section and side views, respectively, of an assembled implant 900. The chondroinductive cap diameter 901 is larger than the osteoconductive base diameter 902. The osteoconductive base height 904 is about one and one half times larger than the chondroinductive cap height 903. Assembled cap pieces 905 and 906 make up cap portion 907 which mates with base portion 908 via interference fit 909.

FIGS. 10A-10D show top, perspective, section and side views, respectively, of an assembled implant 1000. The chondroinductive cap diameter 1001 is substantially or about the same size as the osteoconductive base diameter 1002. The osteoconductive base height 1004 is about one and one half times larger than the chondroinductive cap height 1003. Assembled cap pieces 1005 and 1006 make up cap portion 1007 which mates with base portion 1008 via interference fit 1009.

Figure 11A:
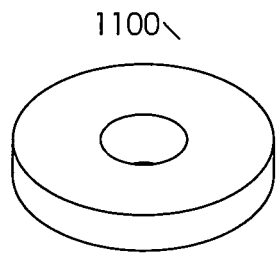
FIG. 11A shows a perspective view of a chondroinductive washer portion.

FIG. 11A shows a perspective view of a chondroinductive washer portion 1100.

FIGS. 11B-11F show a series of cross sectional views of several embodiments of a two part upper washer and lower fixation portion implant. Upper portion 1100 and lower portions 1101 to 1006 may each be formed of various materials including mineralized or demineralized cortical or cancellous bone. Upper portions 1100 are preferably formed of demineralized cortical bone. Lower portions 1101 to 1106 are preferably formed of mineralized cortical or cancellous bone, with the top surface 1107 preferably demineralized or recessed below the upper portion 1100.

Figure 11B:
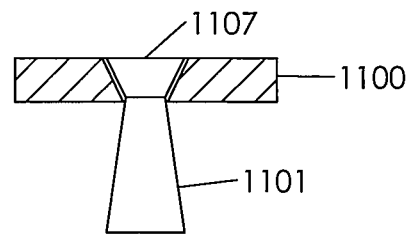
FIGS. 11B-11F show a series of cross sectional views of negatively tapered, non-tapered, positively tapered, threaded and expanding embodiments, respectively, of a hydration controlled interference fit assembled implant, each including a chondroinductive portion assembled with or just above an osteoconductive portion.

FIG. 11B shows a perspective view of a chondroinductive washer portion 1100 together with a negatively tapered osteoconductive fixation portion 1101. The fixation portion 1101 may be physically compressed, dehydrated or force fit into the surgical implantation site.

Figure 11C:
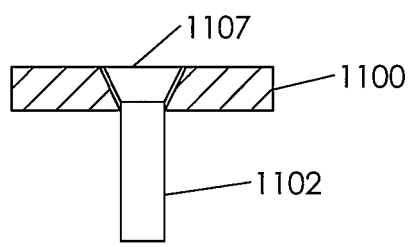

FIG. 11C shows a perspective view of a chondroinductive washer portion 1100 together with a non-tapered osteoconductive fixation portion 1102. The fixation portion 1102 may be physically compressed, dehydrated or force fit into the surgical implantation site.

Figure 11D:
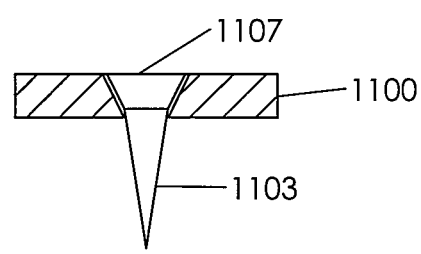

FIG. 11D shows a perspective view of a chondroinductive washer portion 1100 together with a positively tapered osteoconductive fixation portion 1103. The fixation portion 1103 may be physically compressed, dehydrated or force fit into the surgical implantation site.

Figure 11E:
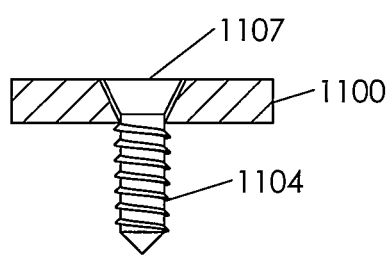

FIG. 11E shows a perspective view of a chondroinductive washer portion 1100 together with a threaded osteoconductive fixation portion 1104. The fixation portion 1104 may be threaded into and physically compressed, dehydrated or force fit into the surgical implantation site.

Figure 11F:
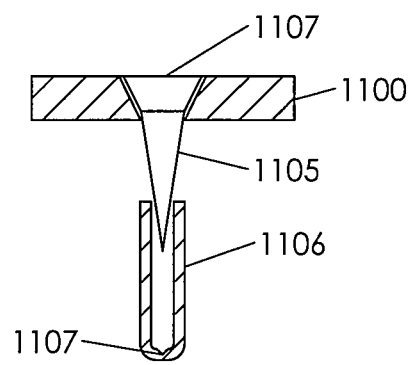

FIG. 11F shows a perspective view of a chondroinductive washer portion 1100 together with a wedge portion 1105 and an expandable osteoconductive fixation portion 1106. The wedge portion 1105 forces the expandable osteoconductive portion 1106 to expand when inserted. Expandable portion 1106 may have stress reliefs or slots 1107 cut at one or more points around its circumference and along its length.

Figure 12A:
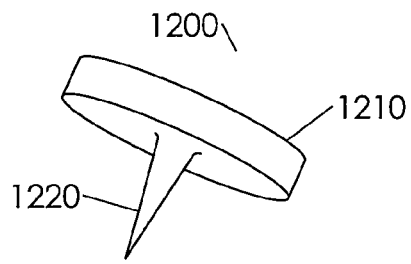
FIG. 12A shows a perspective view of a unitary anchored cap implant, including a chondroinductive portion and an osteoconductive portion.

FIG. 12A shows a perspective view of a unitary chondroinductive anchored cap implant 1200, with a chondroinductive top portion 1210 and an osteoconductive fixation portion 1220.

FIGS. 12B-12F show a series of cross sectional views of several embodiments of a one part anchored cap implant. Upper portion 1210 and lower portions 1221 to 1226 may each be formed of various materials including mineralized or demineralized cortical or cancellous bone. Upper portions 1210 are preferably formed of demineralized cortical bone. Lower portions 1221 to 1226 are preferably formed of mineralized cortical or cancellous bone. A unitary implant having portions of different materials such as mineralized cancellous lower portion and a demineralized cortical upper portion is possible where cortical-cancellous bone material is recovered from a specific anatomic site having both cortical and cancellous bone present, such as an iliac crest or femoral head, processed to preserve and align the natural cortical-cancellous transition, and segmentally demineralized in selected regions or portions, such as a demineralized cortical upper portion.

Figure 12B:
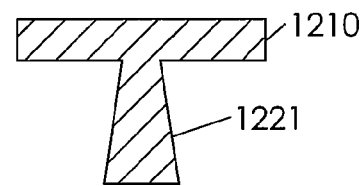
FIGS. 12B-12F show a series of cross sectional views of negatively tapered, non-tapered, positively tapered, threaded and expanding embodiments, respectively, of a unitary anchored cap implant, each including a chondroinductive portion formed together with or just above an osteoconductive portion.

FIG. 12B shows a cross sectional view of a unitary anchored cap implant having a chondroinductive portion 1210 together with a negatively tapered osteoconductive fixation portion 1221. The fixation portion 1221 may be physically compressed, dehydrated or force fit into the surgical implantation site.

Figure 12C:
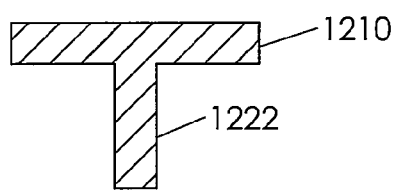

FIG. 12C shows a cross sectional view of a unitary anchored cap implant having a chondroinductive portion 1210 together with a non-tapered osteoconductive fixation portion 1222. The fixation portion 1222 may be physically compressed, dehydrated or force fit into the surgical implantation site.

Figure 12D:
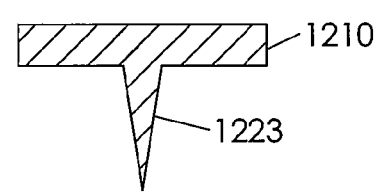

FIG. 12D shows a cross sectional view of a unitary anchored cap implant having a chondroinductive portion 1210 together with a positively tapered osteoconductive fixation portion 1223. The fixation portion 1223 may be physically compressed, dehydrated or force fit into the surgical implantation site.

Figure 12E:
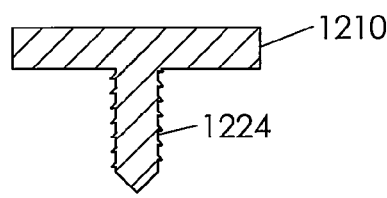

FIG. 12E shows a cross sectional view of a unitary anchored cap implant having a chondroinductive portion 1210 together with a threaded osteoconductive fixation portion 1224. The fixation portion 1224 may be threaded into and physically compressed, dehydrated or force fit into the surgical implantation site. For clarity, the threaded surface is shown in full, non cross section view.

Figure 12F:
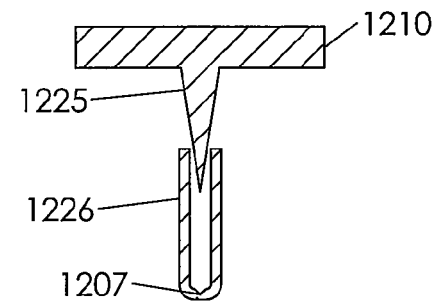

FIG. 12F shows a perspective view of a unitary anchored cap implant having a chondroinductive portion 1200 together with a wedge portion 1225 and an expandable osteoconductive fixation portion 1226. The wedge portion 1225 forces the expandable osteoconductive portion 1226 to expand when inserted. Expandable portion 1226 may have stress reliefs or slots cut at one or more points around its circumference and along its length (not shown).

Figure 13A:
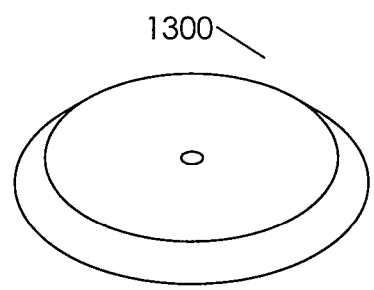
FIGS. 13A-13C show a series of views of relaxed, bent and implanted states, respectively, of a unitary undercut chondroinductive washer implant, each including a chondroinductive portion with an undercut edge and an optional graft manipulation or fixation hole.

FIG. 13A shows a perspective view of a chondroinductive washer implant 1300 in a relaxed or undeformed state.

Figure 13B:
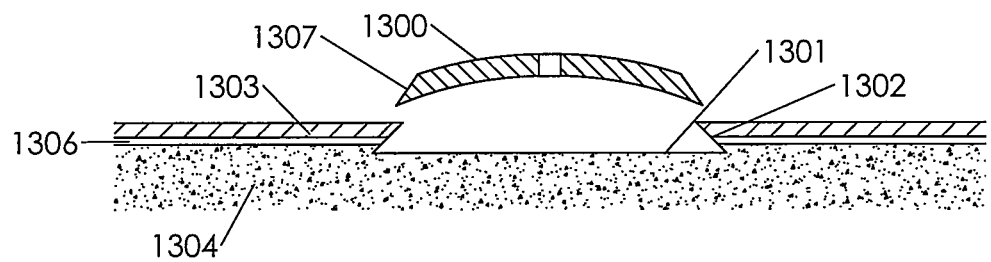

FIG. 13B shows a cross sectional view of implant 1300 in a bent or deformed state and positioned above a surgically created defect 1301 having undercut edge 1302 and extending from cartilage layer 1303, through cortical bone layer 1306 and into subchondral bone layer 1304.

Figure 13C:
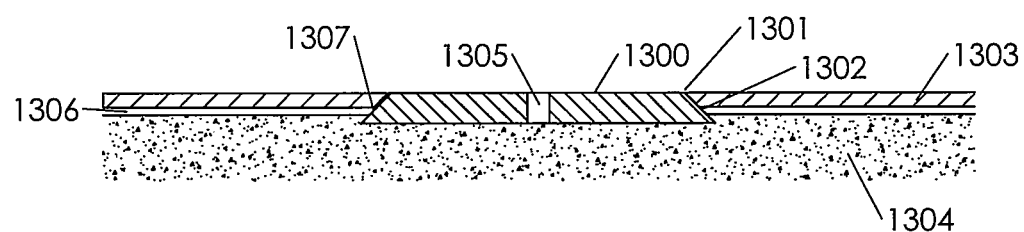

FIG. 13C shows an implanted unitary undercut chondroinductive washer implant 1300, including an undercut implant edge 1307 and a graft manipulation or fixation hole 1305, implanted at a surgical defect site 1301 and filling a cartilage layer 1303 and a subchondral bone layer 1304 of defect 1301, while contacting or anchoring implant edge 1307 at least in part beneath undercut edge 1302.

Figure 14A:
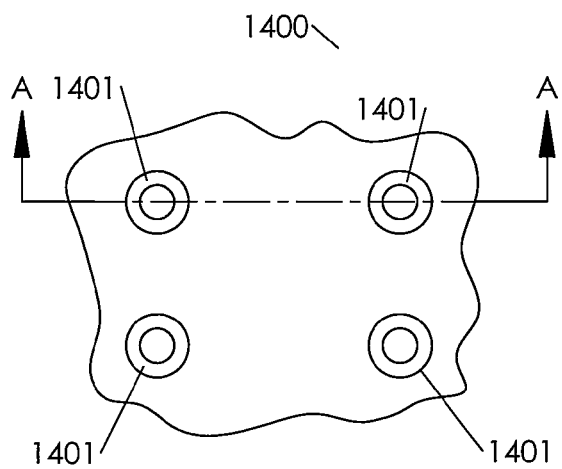
FIGS. 14A-14D show top, perspective, section and side views, respectively, of a chondroinductive membrane implant with pre-machined fixation holes.

FIG. 14A shows a top view of a chondroinductive membrane implant 1400 with pre-machined fixation holes 1401.

Figure 14B:
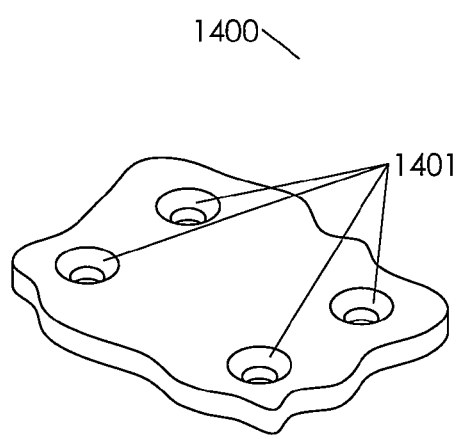

FIG. 14B shows a perspective view of a chondroinductive membrane implant 1400 with pre-machined fixation holes 1401 which may be tapered through part or all of the thickness of the membrane.

Figure 14C:
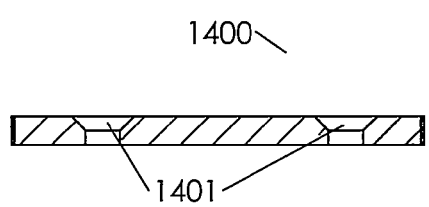

FIG. 14C shows a section view of a chondroinductive membrane implant 1400 with pre-machined fixation holes 1401 which may be tapered through part or all of the thickness of the membrane.

Figure 14D:
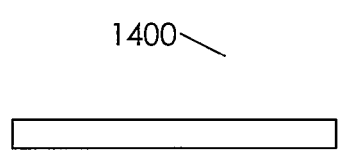

FIG. 14D shows a side view of a chondroinductive membrane implant 1400 in a flat state. Chondroinductive membrane implant 1400 may optionally be produced in a convex, concave or irregular shape (not shown) profile to fit the implant site.

Figure 15A:
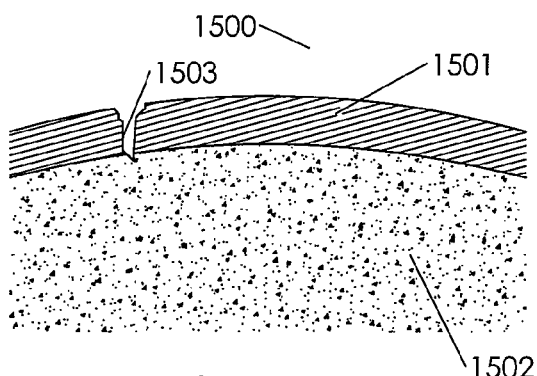
FIGS. 15A-15C show a series of cross sectional views of an osteochondral surgical site for a primary plug procedure (A) in the disease state, (B) after creation of the primary surgical defect or core, and (C) following repair with an implant, respectively, wherein one or more implants are implanted by the present methods.
Figure 15B:
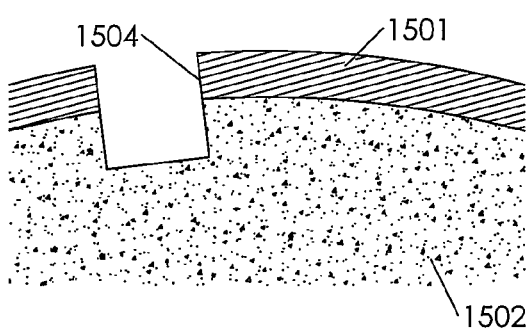
Figure 15C:
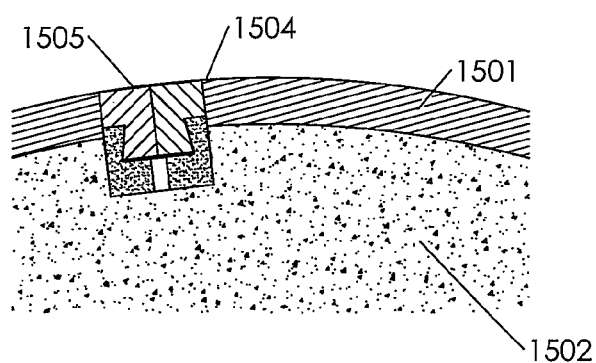

FIGS. 15A-15C show a series of cross sectional views of an osteochondral surgical site for a primary plug procedure (A) in the disease state, (B) after creation of the primary surgical defect or core, and (C) following repair with an implant, respectively, wherein one or more implants are implanted by the present methods.

FIG. 15A shows a section view of an osteochondral defect 1503 at an osteochondral surgical site 1500, extending through a cartilage layer 1501 and into a subchondral bone layer 1502. The thin cortical shell existing between the cartilage layer and subchondral bone layer has been omitted for clarity.

FIG. 15B shows a section view of a surgically created defect or core 1504 extending through a cartilage layer 1501 and into a subchondral bone layer 1502, created by drilling or coring out of defect 1503 from FIG. 15A.

FIG. 15C shows a section view of a bifunctional implant 1505, implanted in a surgically created defect or core 1504 extending through a cartilage layer 1501 and into a subchondral bone layer 1502, created by drilling or coring out of defect 1503 from FIG. 15A.

Figure 15D:
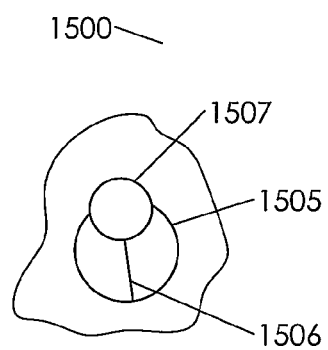
FIG. 15D shows a top or plan view of an overlapping multiple implant configuration ("snowman" configuration).

FIG. 15D shows a top or plan view of a first bifunctional implant 1505 having an assembly seam 1506, implanted at an osteochondral defect site 1500 and a second bifunctional implant 1507 implanted in a snowman configuration, overlapping the first implant 1505 by about one third. The second implant 1507 is located along or in the direction of seam 1506.

FIGS. 16A-16E show a series of section views of an osteochondral surgical site 1600 for a secondary or backfill plug procedure with the defect 1601 in the disease state, after creation of the primary surgical defect or core 1602, after creation of the secondary surgical defect 1603 by removal of the secondary plug core 1604, following repair of the primary defect 1602 with the secondary core 1604, and following repair of the secondary or backfill defect 1603 with a bifunctional implant 1605, respectively, wherein one or more implants are implanted by the present methods.

Figure 16A:
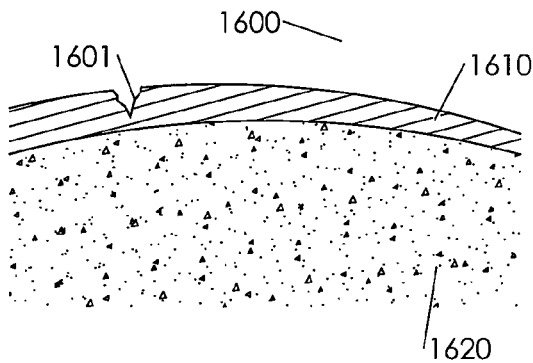
FIGS. 16A-16E show a series of cross sectional views of an osteochondral surgical site for a secondary or backfill plug procedure in the disease state, after creation of the primary surgical defect or core, after creation of the secondary plug core, following repair of the primary defect with the secondary core, and following repair of the secondary or backfill defect with an implant, respectively, wherein one or more implants are implanted by the present methods.

FIG. 16A shows a section view of an osteochondral surgical site 1600 for a secondary or backfill plug procedure with the defect 1601 in the disease state. The defect 1601 extends through the cartilage layer 1610 and into the subchondral bone layer 1620.

Figure 16B:
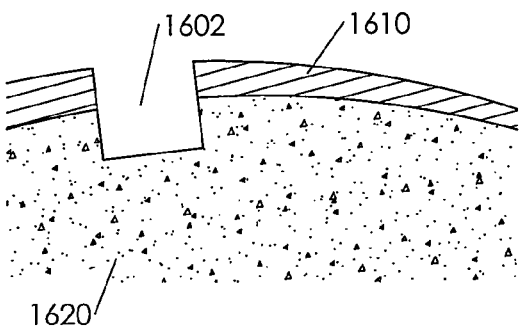

FIG. 16B shows a section view of an osteochondral surgical site 1600 after creation of the primary surgical defect or core 1602, extending through the cartilage layer 1610 and into the bone layer 1620.

Figure 16C:
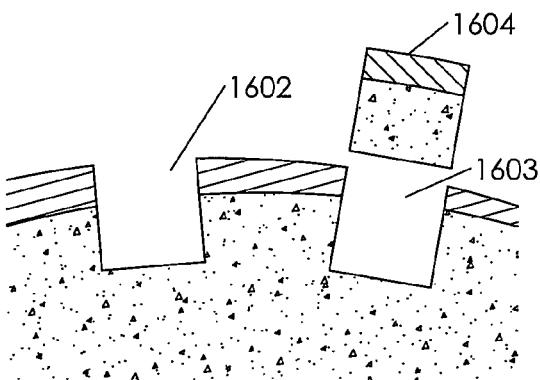

FIG. 16C shows a section view of an osteochondral surgical site 1600 after creation of the secondary surgical defect 1603 by removal of the secondary plug core 1604.

Figure 16D:
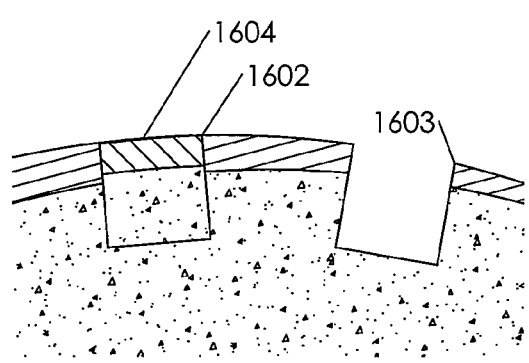

FIG. 16D shows a section view of an osteochondral surgical site 1600 following repair of the primary defect 1602 with the secondary core 1604, which was removed from the secondary or backfill 1603 defect in FIG. 16C.

Figure 16E:
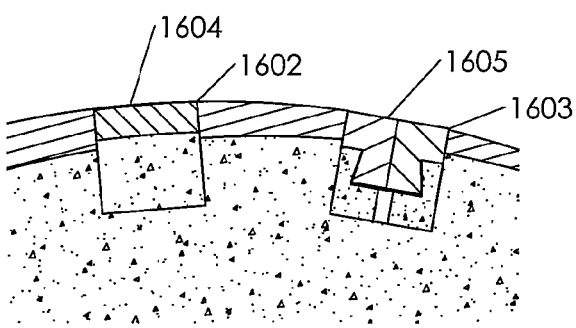

FIG. 16E shows a section view of an osteochondral surgical site 1600 following repair of the secondary or backfill defect 1603 with a bifunctional implant 1605.

FIGS. 17A-17D show a series of orthogonal views and an exploded perspective view of a section of the shaft of a long bone 1700, showing the location for recovery of a blank 1701 to produce a hemi cylindrical cortical bone portion 1702, advantageously producing an implant portion having naturally occurring internal Haversian canals 1703.

FIG. 17A shows a top plan view of a blank 1701 to produce a hemi cylindrical cortical bone portion 1702.

FIG. 17B shows a right side view of a blank 1701 to produce a hemi cylindrical cortical bone portion 1702, advantageously producing an implant portion having naturally occurring internal Haversian canals 1703.

FIG. 17C shows a front view of a blank 1701 to produce a hemi cylindrical cortical bone portion 1702, advantageously producing an implant portion having naturally occurring internal Haversian canals 1703.

FIG. 17D shows an exploded perspective view of a blank 1701 to produce a hemi cylindrical cortical bone portion 1702, cut from a section of the shaft of a long bone 1700 in an axial alignment, advantageously producing an implant portion having naturally occurring internal Haversian canals 1703 aligned with a major body axis of the implant portion 1702.

Figure 18A:
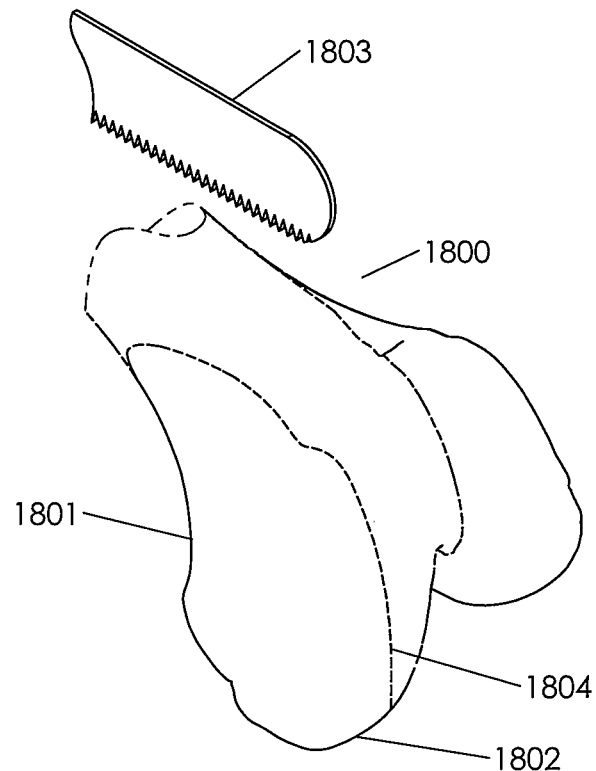
FIGS. 18A and 18B show a series of views of the condyle of a long bone, wherein the cancellous bone source material is recovered, advantageously producing an implant having optimal density and quality of cancellous bone for the formation of an osteoconductive base.
Figure 18B:
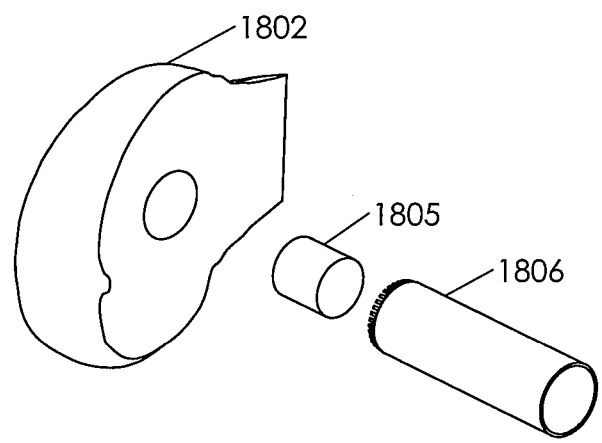

FIG. 18A shows a perspective view and FIG. 18B shows a perspective cross section view of the condyle 1801 of a long bone 1800, wherein the cancellous bone source material is recovered, typically by sawing a rectangular section 1802 with a saw 1803 along cut line 1804 and/or by coring out a cylindrical section 1805 with a coring drill 1806, advantageously producing an implant having optimal density and quality of cancellous bone for the formation of an osteoconductive base.

Figure 19:
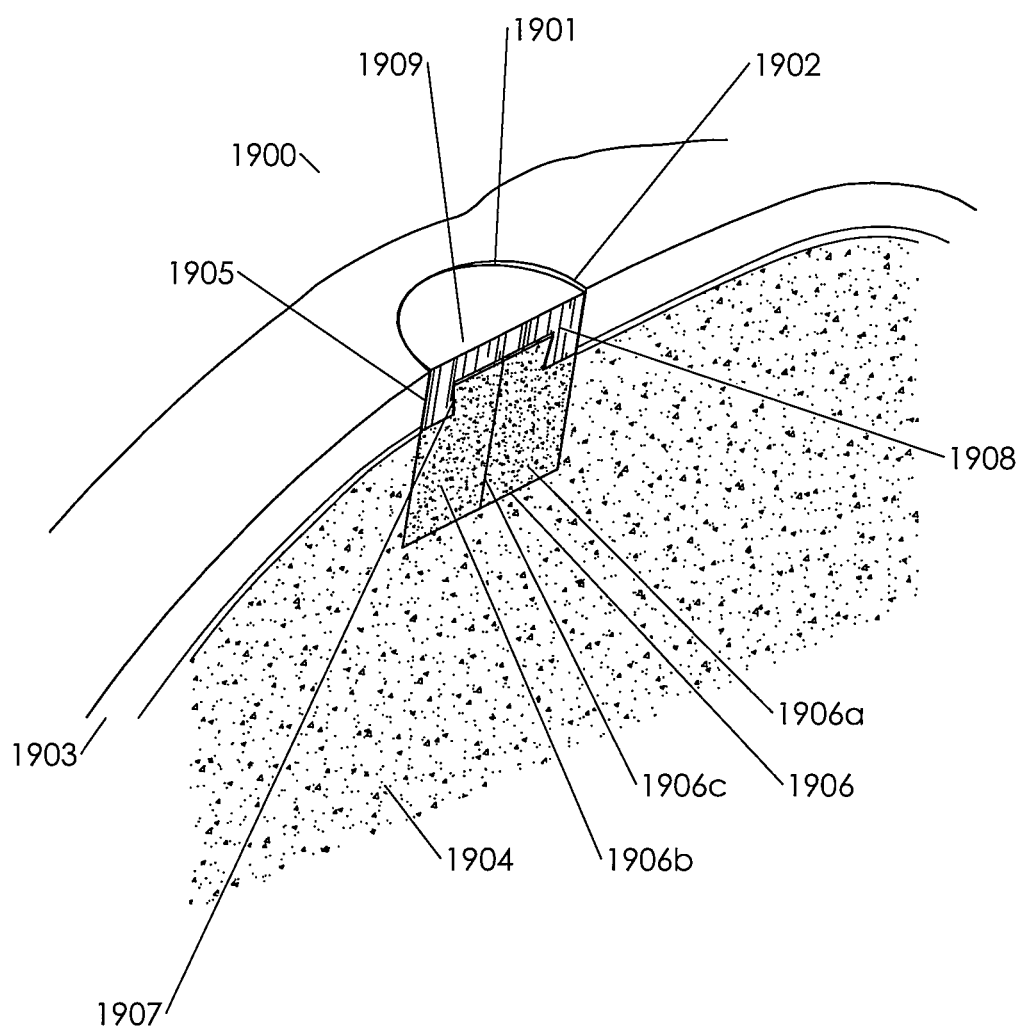
FIG. 19 shows a perspective cross sectional view of an implant implanted at an osteochondral surgical site by the present methods.

FIG. 19 shows a perspective cross sectional view of a cylindrical cartilage repair implant 1901 implanted at an osteochondral surgical site 1900 by the present methods. A surgically created defect 1902 passes through a cartilage layer 1903 and into a subchondral bone layer 1904 of the patient. A chondroinductive demineralized cortical bone cap portion 1905 fills the top region of the surgical defect 1902 within the cartilage layer 1903. An osteoconductive cancellous bone base portion 1906 fills the bottom region of the surgical defect 1902 within the subchondral bone layer 1904. Base portion 1906 is assembled from two pieces 1906a and 1906b, which meet at seam 1906c, visible through the cross section. A negatively tapered shaft and bore interference fit holds pieces 1906a and 1906b together with cap 1905. Natural Haversian canals 1908 are substantially in alignment with the major axis of implant 1901 and in communication between base portion 1906 and top surface 1909 of cap portion 1905.

In one embodiment the assembled implants include a chondroinductive portion having a characteristic width or diameter which is substantially the same as a characteristic width or diameter of an osteoconductive portion, providing for a uniform fit and easy insertion at a osteochondral defect site.

In another embodiment the assembled implants include a chondroinductive portion having a characteristic width or diameter which is larger than a characteristic width or diameter of a corresponding osteoconductive portion, providing for an oversized chondroinductive portion and tight fit with the cartilage layer upon insertion at a osteochondral defect site, such as a surgically created defect site.

In another embodiment the assembled implants include a chondroinductive portion having a characteristic width or diameter which is smaller than a characteristic width or diameter of a corresponding osteoconductive portion, providing for an oversized osteoconductive portion and tight fit with the subchondral bone layer upon insertion at an osteochondral defect site. This oversized osteoconductive portion has the added advantage of insertion into the defect site without direct compression of or damage to the chondroinductive portion.

In one embodiment, an assembly includes at least one osteoconductive cancellous xenograft bone portion and at least one chondroinductive cortical allograft bone portion. In an alternative embodiment, an assembly includes at least one osteoconductive cancellous allograft bone portion and at least one chondroinductive cortical xenograft bone portion. Preferably, the xenograft bone portion in either embodiment is treated to remove blood, fat, lipids, antigens, unattached proteins or a combination of these.

The present implants may optionally be provided with a second chondroinductive portion which is adapted for insertion around the primary implant at the osteochondral defect site. This second chondroinductive portion may either be assembled or not assembled to the primary implant prior to insertion, and having the same or different properties with respect to source material, mineralization, hydration state, or orientation of Haversian canals. This second chondroinductive portion fits around the first chondroinductive portion and fills any potential gap between the implant and the surrounding articular cartilage and provides for improved healing, remodeling and regeneration of the cartilage. This second chondroinductive portion may take the form of a concentric cylinder or partial cylinder around, on top of or overlapping the first chondroinductive portion.

In an alternative embodiment of the implants of the present invention, an elongate cortical bone portion, preferably a cylindrical portion, is taken from a long bone, preferably from the diaphysis of a long bone, in an orientation resulting in substantial alignment between a major axis of the elongate cortical bone portion and the primary direction or orientation of the naturally occurring Haversian Canals in the long bone. This produces an elongate bone implant with canals oriented along its length, substantially parallel to a major body axis of the implant. This all cortical implant is preferably of unitary construction and taken from a single core or piece of bone. One end of the elongate or cylindrical cortical bone implant is then substantially demineralized to produce a chondroinductive demineralized cortical bone portion. The opposing end of the implant is maintained in a mineralized, lightly demineralized, or partially demineralized state. The cortical bone structure at this second end, either mineralized, lightly demineralized or partially demineralized, provides an osteoconductive cortical bone portion. Alternatively, the opposing end of the implant is also substantially demineralized, with the central region of the implant maintained in a mineralized, lightly demineralized, or partially demineralized state.

In yet another alternative embodiment an elongate cortical bone portion, preferably a cylindrical portion, is taken from a long bone, preferably from the diaphysis of a long bone, in an orientation resulting in substantial alignment between a major axis of the elongate cortical bone portion and the primary direction or orientation of the naturally occurring Haversian Canals in the long bone. This produces an elongate bone implant with canals oriented along its length, substantially parallel to a major body axis of the implant. This all cortical implant is preferably of unitary construction and taken from a single core or piece of bone. Most or all of the elongate or cylindrical cortical bone implant is then substantially demineralized to produce a chondroinductive demineralized cortical bone cartilage repair implant.

In one embodiment, an elongate cortical bone implant is provided having a cylindrical, rectangular, elliptical, oval or egg shaped body with sides which are either rectilinear or arcuate, and may be convex, concave or substantially flat across all or a portion of their length. The implant of this embodiment is formed substantially from cortical bone, having a major body axis running along its length, and is preferably recovered from the diaphysis of a long bone such that the naturally occurring Haversian canals of the cortical bone material are in substantial alignment with a major body axis of the implant, and/or in communication with one or more end surfaces of the implant. The end surfaces may be flat, concave or convex. The implant of this embodiment is typically demineralized at one end, alternatively demineralized at both ends or along most or all of the entire length of the implant. The demineralization may vary along the length of the implant. For example, the implant may be substantially demineralized at a first end and partially demineralized at a second end, with either a sharp transition or a broad zone of transition between the substantially mineralized and partially mineralized portions. Preferably, the implant is a unitary implant mineralized along one-half to two-thirds of its length and demineralized along one-third to one-half of its length.

These unitary implants may have negatively tapered, non-tapered, positively tapered, threaded or expanding osteoconductive fixation portions that allow for fixation in the surgical site. Expandable portions may have stress reliefs or slots cut at one or more points around their circumference and along their length. The fixation portion may be physically compressed, threaded, dehydrated or force fit into the surgical implantation site.

The present invention also provides a method of using an assembled cartilage repair implant to treat a cartilage defect in a mammal, including filling an osteochondral defect having a subchondral bone layer and a cartilaginous layer with an assembled implant adapted for implantation into a bone cartilage junction, wherein the assembled implant has at least one osteoconductive cancellous bone portion and at least one chondroinductive cortical bone portion. In this method the subchondral bone layer of the defect is filled with the osteoconductive portion and the cartilaginous layer of the defect is filled with the chondroinductive cortical bone portion.

The present disclosure also describes an assembled cartilage repair implant, suitable for implantation at an osteochondral site in a human patient, and assembled via an interference fit, having at least one osteoconductive cancellous bone portion and at least one chondroinductive demineralized cortical bone portion, wherein the osteoconductive portion and the chondroinductive portion are assembled in a stacked relationship. The hydration controlled interference fit is preferred because it allows a solid connection between an osteoconductive base portion and an chondroinductive cap or top portion. A hydration controlled interference fit is especially preferred when the chondroinductive top portion is assembled from two or more pieces of demineralized cortical bone, because it can be configured to hold the two or more pieces together in alignment and prevent separation or displacement of the two or more pieces.

The present disclosure also describes an implant adapted for implantation at an articulating cartilage site, with a chondroinductive membrane of demineralized cortical bone, including natural canals oriented across the thickness of the membrane and providing natural porosity, at least one machined, formed or punched hole adapted to receive a fixation device such as suture, a pin, a staple, or a bone pin, and a flat, smooth or convex upper surface, adapted to approximate the surface geometry of an articulating cartilage site.

In an alternative embodiment, the membrane is recovered, preferably from a long bone, in a radial section wherein the Haversian canals are oriented at an oblique angle or transverse to the thickness of the membrane, typically running along either the length or width of the membrane, or both. In this alternative embodiment, membrane porosity can be provided by perforations or holes drilled, punched, etched or otherwise formed across the thickness of the membrane, preferably after demineralization, to provide a chondroinductive membrane.

In another embodiment an implant adapted for implantation at an articulating cartilage site is provided, having a membrane of demineralized cortical bone, including natural Haversian canals oriented across the plane of the membrane. Natural Haversian canals oriented generally across or at substantial angle to the plane of the membrane may advantageously provide transport, signaling, and growth pathways across the thickness of the membrane to support ingrowth, chondroinduction and chondroconduction.

A "membrane" is a flexible or semi-flexible matrix whose length, diameter and/or width is greater than its thickness, typically at least about 2 times greater, preferably at least about 5 times greater, alternatively at least about 10 times greater. A membrane may be used to withstand physiological loading and maintain structural support while allowing or facilitating transport of specific cell or fluid types, such as large or small cells, water or blood. A membrane may be secured by physical fixation, by design of the surrounding implantation site, or by chemical or biological adhesives, glues or other chemical bonding agents. A membrane may be secured at one or more points near its center or along its edges or both. A preferred embodiment is a membrane which has a thickness which is constant or varies across its length and width, within a range between about 0.5 mm and about 5 mm.

One embodiment of a membrane is a "washer", typically secured by a single means of physical fixation at or near its center, alternatively secured by one or more fixation devices along its periphery. A washer is typically between about 4 mm and about 12 mm in width or diameter, is preferably circular, and may be formed flat or concave or convex to approximate the geometry of the intended implantation site.

An "anchored cap" implant is typically a unitary construct including a chondroinductive cap portion and an osteoconductive anchoring portion. The cap portion is typically larger in diameter, length or width than the anchoring portion, preferably at least about 2 times larger, optionally at least about 4 times larger, also optionally at least about 8 times larger. One embodiment of an anchored cap is preferably formed of cortical bone, and demineralized or partially demineralized in the chondroinductive cap region, optionally lightly demineralized, partially demineralized, or fully demineralized in the anchoring region. Another embodiment of an anchored cap is formed of a biocompatible polymer or other synthetic composition, optionally with the same or different material properties or composition in the cap region and anchoring region. The anchoring region is typically deeper or longer than the thickness of the cap region, preferably at least about two times longer, optionally at least about 4 times longer, also optionally at least about 8 times longer.

A "bifunctional implant" is one which is effective to provide two different environments or supports for two types of tissue growth, regeneration, or repair. For example, a bifunctional implant may promote two types of tissue growth such as cartilage regeneration and bone regeneration adjacent to or at the same implant site. The bifunctional implant will typically have two distinct portions or regions.

An implant or portion is "osteoconductive" when it has the ability to serve as a scaffold to promote the growth or formation of bone, forming healthy new bone tissue, bony tissue, or bone forming cells throughout or along at least a portion of the scaffold.

An implant or portion is "osteoinductive" when it has the capacity to stimulate or promote the growth or formation of bone, forming healthy new bone tissue, bony tissue, or bone forming cells where such tissue otherwise would not form, such as by inducing the growth, maturation, reproduction or activity of stem cells, osteoblasts or any other cells that cause or contribute to the formation of bone.

In many of the embodiments described herein, certain elements are described as osteoconductive, but other embodiments are also contemplated where like elements are osteoinductive instead of or in addition to being osteoconductive.

"Cartilaginous tissues" include cartilage, articulating cartilage, hyaline cartilage, elastic cartilage, fibrocartilage and cartilage-like tissues.

An implant or portion is "chondroinductive" when it has the capacity to stimulate or promote the growth or formation of cartilaginous tissues where such tissue otherwise would not form, such as by inducing the growth, maturation, reproduction or activity of stem cells, fibroblasts, muscle cells or any other cells that cause or contribute to the formation of cartilaginous tissues.

An implant or portion is "chondroconductive" when it has the ability to serve as a scaffold to promote the growth or formation of cartilaginous tissues, such as by regeneration of cartilage or cartilage cells, forming new cartilaginous tissues, or cartilage forming cells throughout or along at least a portion of the scaffold.

In many of the embodiments described herein, certain elements are described as chondroinductive, but other embodiments are also contemplated where like elements are chondroconductive instead of or in addition to being chondroinductive.

A "stacked relationship" means two or more pieces are arranged in contact with one another, such as where a first piece is at least partially on top of or disposed upon a second piece. A preferred stacked relationship is where two pieces are in contact with one another in an axial orientation with respect to a central axis of one of the pieces or of the combined assembly. In a simple form a stacked relationship exists between two or more substantially flat, rectangular, disk shaped, or planar portions with a given thickness, arranged one on top of the other. In some cases a stacked relationship includes two or more portions which overlap, interdigitate, protrude into, partially surround or otherwise interact with each other. A child's building block set, where stacked pieces snap together through interlocking or interdigitating features would be one example of such a stacked relationship. A stacked relationship may include two or more stacked layers. A "layer" may include one or multiple adjacent portions or pieces that make up that layer. The individual adjacent portions or pieces combine to form the layer, and each adjacent portion may interface with one or more portions in the next stacked layer. Geometric features from a given portion in any layer may extend into other layers. A stacked relationship may also exist between 3 dimensional shaped portions with flat, ridged, toothed, textured, planar, non-planar, arcuate, non-arcuate, polyhedral, or other surfaces making up the interface between any two portions.

Starting Materials and Procedures

Sources of material for the present implants include crosslinked or non-crosslinked autograft, allograft, and xenograft bone; as well as crosslinked cartilage, tendon, ligament, muscle, or other connective tissue of autograft, allograft, or xenograft origin. Soft or connective tissues, unlike bone tissues, are generally used in conjunction with other materials or otherwise processed to provide the levels of strength and stiffness required by surgical constraints and anatomical remodeling processes. Sources of material for the present implants also include hydroxyapatite, tricalcium phosphate, calcium sulfate or other synthetic or natural calcium compounds, ceramics, other chemical compounds or polymers known to approximate or mimic certain features of natural bone or cartilage, or to be biocompatible, bioabsorbable, or bioresorbable.

The present implants may be made from source material including autograft bone, allograft bone, xenograft bone, or a combination thereof. In some instances it is advantageous to provide an implant assembled from components having the same or different source materials. For example, allograft bone can be more chondroinductive than untreated xenograft bone. In contrast, xenograft bone which has been treated to reduce inflammation and antigenicity may be equally or more chondroinductive as compared to allograft bone.

Allograft bone is advantageous for its lack of immune response, rapid incorporation and natural presence of growth factors encouraging osteoinduction or chondroinduction. Xenograft bone is advantageous for its availability, similarity to allograft bone, and for its greater availability of larger sizes and certain geometric configurations. Autograft bone is advantageous for its lack of inflammation, possible presence of living cells, and rapid remodeling in the host. Autograft bone is less practical due to concerns over harvest-site morbidity, additional complication and costs associated with interoperative tissue recovery, and logistical challenges for processing (for example, machining or sterilizing) in the operating room.

In some embodiments, materials for an assembled implant are selected from different source materials. In assembled embodiments, different materials are advantageously selected for individual components. In one embodiment, a xenograft cancellous base provides an osteoconductive lower portion, while an allograft demineralized cortical bone cap provides a chondroinductive upper portion. Xenograft tissue is more readily available, and when properly treated to remove or reduce antigenicity, may provide a structural osteoconductive matrix for remodeling. Allograft bone tissue contains a mix of naturally occurring growth factors in a collagen matrix to support chondroinduction and remodeling. In another embodiment, a hydroxyapatite base provides an osteoconductive lower portion, while an allograft demineralized cortical bone cap provides a chondroinductive upper portion. In another embodiment, a hydroxyapatite base provides an osteoconductive lower portion, while a polymeric cap optionally seeded or provided with one or more growth factors, cells or nutrients provides a chondroinductive upper portion. In a particularly preferred embodiment an allograft mineralized cancellous base provides an osteoconductive lower portion, while an allograft demineralized cortical bone cap provides a chondroinductive upper portion.

When the source material is a natural bone tissue such as autograft, allograft or xenograft bone, the selection of a specific type of bone tissue may be advantageous for a given application.

The demineralized cortical bone portions of the present implants may be made up of from one to sixteen pieces of cortical bone, alternatively from two to eight pieces of cortical bone, alternatively from two to four pieces of cortical bone, preferably from one, two, or three pieces of cortical bone, more preferably from a single piece of cortical bone or from two pieces of cortical bone. A portion made up of two pieces of cortical bone is advantageous because it provides optimal yield for intermediate to large implants, especially given the anatomical constraints of allograft tissue and limited availability with the proper orientation of naturally occurring Haversian canals, along with a relatively simple mechanical design and assembly. A portion made up of a single piece of cortical bone is advantageous because it provides simplicity, reliability, ease of manufacture and robustness in-situ during remodeling. A portion made up of one, two or three pieces of cortical bone is advantageous because it provides a balanced and flexible set of options to produce suitable numbers of implants, with relatively simple design and high reliability from the available bone supply. A portion having from one to sixteen, two to eight, or two to four pieces of cortical bone is desirable because it provides multiple options in the design and fabrication of suitable implants from the available bone supply, and especially from smaller bone pieces.

Cortical bone material taken from the central axial region or diaphysis of a long cortical bone naturally includes a series of canals, these Haversian canals being oriented in a direction providing transport along the axial direction of the long bone. These natural constructs within the collagen matrix of the bone are well suited not only for transport of blood, cells and proteins, but also for cell proliferation and attachment critical to the early stages of either chondroinduction or osteoinduction. In one embodiment the present implants advantageously provide cortical bone pieces or portions having internal canals, preferably the naturally occurring Haversian canals, specifically oriented in a direction which provides transport between the outside of the graft or an outer surface of the cortical bone piece or portion, and the inside of the graft or an inner surface of the cortical bone piece or portion or to an interface of a cortical bone piece or portion and a cancellous bone piece or portion. This is particularly preferred where the porous cancellous bone is intended for implantation at a prepared surgical site in contact with the bloody surface of a prepared osteochondral defect providing blood, cells, nutrients, proteins and the like to the implant. The orientation of the canals can advantageously support and enhance the flow of blood, cells, nutrients, proteins and the like into the cortical bone matrix to enhance chondroinduction. Alternatively, the canals are advantageously oriented to provide transport between any first surface of a piece or portion of cortical bone and any second surface of a piece or portion of cortical bone.

In one embodiment, cortical bone material is selected from a transverse cut through the diaphysis of a long bone, such that the fiber orientation and the orientation of the Haversian canals within the cortical bone portion is aligned in a substantially perpendicular orientation with respect an outer face of the cortical bone portion. In this embodiment, the cortical bone portion is assembled to the cancellous bone portion such that in the final assembly the naturally occurring canals within the cortical bone portion are in communication between an external surface of the cortical bone portion and an internal surface of the cortical bone portion, wherein that internal surface of the cortical bone portion is in contact with an internal surface of the cancellous bone portion. Thus, the canals form a conduit or parallel series of conduits from the outer surface of the cortical bone portion, to an inner surface of the cancellous bone portion. These conduits allow cells, blood, and nutrients from the host body to more readily reach the interstices of the cortical bone portion after passing through the porous structure of the cancellous bone portion, thereby increasing the ability of the cortical bone portion to remodel within the host after implantation, especially when the implant is placed into the recipient such that the cancellous portion is in contact with a prepared defect site or vascularized bed of native cancellous or osteochondral tissue.

An alternative embodiment may be preferred when naturally occurring Haversian canals of the proper orientation are not available due to use of non-bone material, geometric or design constraints of the implant, or availability of diaphysial cortical bone of the proper shape, size and orientation. In this alternative embodiment, canals are created in the cortical bone or non-bone material by techniques such as drilling, punching, etching, salt leaching, nano-fabrication or other suitable methods. Surprisingly, it has been found that machining or drilling of artificial canals prior to demineralization removes chondroinductivity, while machining or drilling of artificial canals after demineralization actually maintains or promotes chondroinductivity. This is contrary to common practice and known methods of machining, where bone is usually cut in a mineralized state to provide support and prevent damage to the underlying collagen matrix and demineralized after machining. While the inventors do not intend to be bound by theory, it is thought that heating or other changes during the machining of mineralized bone is detrimental to growth factors and/or changes surface properties of collagen in a way which jeopardizes signaling events that stimulate chondrogenesis or chondroinductivity.

The source tissue can be treated, such as by demineralization. A bone tissue is fully mineralized when it has not been treated to remove any of the naturally occurring mineral content, and thus contains about 100% of the naturally occurring residual calcium content by weight. A bone tissue is substantially mineralized when it contains at least about 90% residual calcium content by weight, alternatively at least about 95%, alternatively about 100%. Generally, a substantially mineralized bone structure exhibits sufficient mechanical strength and dimensional stability to withstand a press fit or interference fit in a surgical implantation site, and to allow remodeling without excessive subsidence of the bone structure under anatomical loading conditions at a given surgical site.

The desirable range for calcium content in the substantially demineralized bone may vary with specific application and geometry of a given embodiment. Demineralization is typically achieved by an acid driven reaction-front process, wherein the demineralization progresses in a "front" at a known uniform rate from all external surfaces contacted by the acidic medium. A uniform spherical bone portion completely submerged in excess acid will undergo a uniform and symmetric demineralization as the reaction front moves at a constant rate inward from the outer surface toward the center. An irregularly shaped bone portion, e.g., one with protrusions, channels or sharp corners, will have thinner areas where the reaction fronts from opposing surfaces cross over, completely demineralizing the thinner region, before the reaction fronts in thicker regions have completely demineralized those regions. This results in discrete regions of mineralized bone within a partially demineralized bone portion. These mineralized regions are hard, stiff, non-compliant, and may be more osteoinductive than the demineralized regions surrounding them.

A bone tissue is lightly demineralized when 90% or more of its total volume remains mineralized. A bone tissue is partially demineralized when between 90% and 10% of its total volume remains mineralized. A bone tissue is substantially demineralized when less than 10% of its total volume remains mineralized. For example, a substantially demineralized bone has a mineralized volume that is less than about 5% total volume, preferably less than about 1%, more preferably less than about 0.1%, alternatively less than about 0.01%.

Generally, a substantially demineralized bone portion has a residual mineral content that does not noticeably impede the chondroinductivity of the implant, significantly obstruct the mechanics and load bearing of the implant in-situ, or unduly interfere with the manufacturing or surgical implantation processes for that implant.

In making bone implants, cortical bone is often used in a mineralized state for its stiffness and structural properties. However, in making the present implants, substantially demineralized cortical bone is preferred because it more closely approximates the physical properties of cartilage and because it is chondroinductive. In making bone implants, mineralized or demineralized cancellous bone is often used as a non-structural filler material to provide a bone ingrowth path. However, in making the present implants, mineralized cancellous bone is preferred as a structural graft element since it provides osteoconductivity in a matrix whose properties match that of the native subchondral bone.

When the source material includes hydroxyapatite, tricalcium phosphate, calcium sulfate or other synthetic or natural calcium compounds, implants may be formed by methods such as salt leaching and sintering. These materials have osteoconductive properties in certain configurations.

When the source material includes ceramics, other chemical compounds, synthetics or polymers known to approximate or mimic certain features of natural bone or to be biocompatible, bioabsorbable, or bioresorbable, suitable materials may include bioactive glass, PLA, PGA, PLLA, PGLA and other materials known to be suitable for human implantation.

Various materials will have different shrinkage and swelling characteristics. In some cases these material properties are known and published, while in other cases these material properties are determined by laboratory measurement. The present methods can be applied even to materials having unusual material properties, such as materials which shrink upon hydration or have very low or very high, highly anisotropic, or non-reversible ratios of shrinkage or swelling due to hydration or dehydration.

Material properties such as hydration related shrinkage and swelling are anisotropic in some materials, particularly those having a specific fiber or grain orientation such as that found in natural bone. For example, the shrinkage properties of a natural bone portion selected from a long bone are greater across the radial direction of the long bone, and lesser across the axial direction.

Material properties such as hydration related shrinkage and swelling may be altered by the condition or processing of the material. For example, bone can be made to have a higher degree of shrinkage or swelling by removal of an amount of the natural calcium content through acid demineralization or other methods.

Implant Design and Assembly

In some embodiments, the implants or a portion or piece of the implants have a characteristic dimension, such as depth, thickness, width or length. When an implant, portion or piece has a characteristic dimension, it has that dimension in a significant or relevant part or degree, including but not limited to having that dimension uniformly (for example, a uniform depth, uniform thickness, uniform width or uniform length). Alternatively, a characteristic dimension is determined from an average or weighted average across an area or volume, or along another dimension.

In some embodiments, the implants have a thickness or other dimension which varies across their length and width. The thickness of the implant may be optimized to approximate, be less than or exceed the depth of the articulating cartilage layer or cartilaginous tissue layer, or to approximate, be less than or exceed the overall depth of the surgical implantation site or surgically created defect. Typically the overall implant thickness is within a range between about 0.3 mm and about 10 mm, alternatively between about 0.5 mm and about 5 mm, preferably between about 1 mm and about 4 mm, also preferably between about 2 mm and about 3.5 mm.

In some embodiments of the present implants and methods, two or more components are assembled together by interference fitting, such as by hydration controlled shrink fitting. "Hydration controlled interference fit" refers to a condition where one or more of the geometric dimensions of one or more portions are controlled at least in part by the addition or removal of moisture (usually water but possibly blood, saline or another fluid) during the manufacturing or assembly process, to produce an advantageous interference fit in the finished assembly or sub-assembly. In one example, a shaft is created on a first portion at a size which is nominally slightly larger than a corresponding bore in a second portion, as measured in the hydrated state. Either one or both of the first and second portions are then dehydrated, wherein the resulting shrinkage of one or both portions produces a shaft which is slightly smaller than the corresponding bore, as measured in the dehydrated state. This is referred to as a clearance fit condition. The two portions are easily assembled in the clearance fit condition. Following assembly, the dehydrated portion(s) are fully hydrated to return them to their hydrated dimensions and to form an interference fit. This is referred to as an interference fit condition. In this way, an interference fit is achieved without subjecting either portion to the stresses and deformations associated with a mechanical press fit, or the unwanted effects of thermal gradients required for a heat controlled interference fit. The end result of assembly in a clearance fit condition, followed by shrinkage and/or swelling, resulting in an interference fit condition is a shrink fit.

A hydration controlled shrink fit is a type of hydration controlled interference fit, and is particularly useful because it joins two pieces together firmly, obtains a high degree of interference and exhibits less damage to and stress in the two assembled parts, as compared to a press fit or other known methods of joining parts together.

Hydration controlled shrink fits and hydration controlled interference fits are especially advantageous when working with materials which are porous, brittle, pliable or easily deformed during a press fit operation. Bone, and especially demineralized bone material, is particularly well suited to the present hydration controlled interference fit assembly methods. Other materials such as bone substitutes, ceramics and polymers are also well suited to these methods. Some polymers, for example, have been shown to have comparable mechanical properties and pullout strength as compared to a cancellous bone material. Cancellous bone is the preferred material for the present implants due to its natural structure which facilitates osteoconduction, healing and remodeling.

The present methods are especially advantageous when assembling together two or more pieces where the mating surface of a first piece is harder, more brittle or less compliant and the mating surface of a second piece is softer, more pliable or easily deformed. When dissimilar materials are assembled in a press fit, damage typically occurs to the softer or more ductile of the two materials, resulting in reduced interference and a looser or less secure fit. The hydration controlled interference fit avoids this potential damage, resulting in a stronger or tighter fit and assembly. The hydration controlled interference fit is advantageous when assembling any demineralized bone together with any mineralized bone, and especially advantageous when assembling demineralized cortical bone together with mineralized cancellous bone.

Alternatively, it is possible to combine elements of hydration controlled shrink or interference fits together with other methods, such as a more traditional press fit or thermally controlled interference fit, to achieve a desired result. For example a shaft and bore press fit requiring 0.15 mm nominal diametrical interference is modified or replaced with a hydration controlled interference fit, allowing for 0.05 mm actual interference during the dehydrated press fit assembly operation, but resulting in an effective interference of the desired 0.15 mm interference following rehydration. This would subject the components to considerably lower stresses and deformations during the press fit assembly operation, while achieving a higher level of interference and tight fit in the final assembled implant.

The application of hydration controlled interference fit is dependent upon several factors, including mechanical design of each portion, material selection, material condition and orientation, order and selection of steps in the manufacturing and assembly process, and selection of suitable manufacturing methods.

Each portion must be given a mechanical design which will allow the hydration related shrinkage and swelling effects. Outside dimensions such as shaft diameters will generally shrink, while inside dimensions such as hole or bore dimensions will generally grow upon dehydration. Larger bodies generally have a greater total shrink, warp or distortion than smaller bodies. However, smaller bodies may have a larger percentage shrink, warp or distortion than larger bodies, especially if they have long, thin or irregular geometric features. Different specific effects typically occur around sharp corners or complex geometric features. Variances in dehydration shrinkage may result in significant warpage or change of shape in a dehydrated body, however bodies will typically return substantially to their original net shape upon rehydration. While it is contemplated that one or both parts of an assembly contribute to a hydration controlled interference fit, it is also contemplated to mate one hydration swellable part to a second non-swellable part. For example, a demineralized cortical bone piece could be mated to a titanium piece to form a hydration controlled interference fit.

In some preferred embodiments, parts are assembled from two different source materials, such as demineralized cortical allograft bone and mineralized cancellous allograft bone, in a shaft and bore fit. In these embodiments the shaft is created on one component as a standing protrusion or boss, and may be straight, positively tapered, or negatively tapered. A positive taper results in a cone, frustoconical or truncated cone protrusion. A negative taper results in tapered undercut or dovetail protrusion. The shaft and bore may also be stepped, providing a tapered or non-tapered undercut or locking feature. When the corresponding bore is created with a positive taper, a tapered hole results, mating with the truncated cone of a positively tapered shaft. When the corresponding bore is created with a negative taper, an undercut hole results, mating with the tapered undercut or dovetail of a negatively tapered shaft. When either the shaft or the bore is made without a taper, a straight cylindrical shaft or bore results. It is contemplated to mix positively, negatively, or non-tapered shafts and bores to create a desired fit geometry for a hydration controlled interference fit or shrink fit. A particularly preferred embodiment includes the negatively tapered shaft and bore hydration controlled shrink fit.

Within shaft and bore fits, the shaft and the bore may have a round, oval, polygonal, irregular, flattened, keyed, or irregular shape. In some embodiments a shaft of a first shape is mixed with a shaft of a second shape. In a particular embodiment a round or cylindrical shaft has material removed from one side to produce a flattened shaft. The flattened shaft then mates with a cylindrical bore, or optionally a flattened cylindrical bore, to produce a shaft and bore fit. This fit has the advantages of a single orientation for assembly and resistance to rotation from that orientation. In another specific embodiment a polygonal shaft is provided to mate with a cylindrical bore. This embodiment has the advantages of controlled and focused stress distribution and greater tolerance for variances in manufacturing or shrinkage processes. In a preferred embodiment a cylindrical shaft mates with a cylindrical bore, with both shaft and bore optionally tapered, concentrically joining two cylindrical pieces together. This embodiment has the advantage of ease of manufacture and assembly, no stress concentrations, and no requirements for angular or rotational alignment during assembly or in use. In all shaft and bore fits, it is contemplated that either the shaft or the bore may be assembled from two or more pieces to form a larger portion or segment.

Similar to the shaft and bore fits, protrusion and slot fits are another type of fit that may be employed instead of or in combination with a hydration controlled interference fit or shrink fit, formed by providing a raised boss or protrusion on one piece for assembly with a cut slot or keyway on a mating piece. Protrusion and slot fits may be straight, positively tapered, or negatively tapered, with constant or varying profiles which are rectilinear, arcuate, irregular, or any combination of these in cross section.

Multiple fits of any kind are contemplated for use within a single assembled implant. In one embodiment two oval shaft and bore fits provide redundancy and alignment to a cylindrical implant. In another embodiment an array of two or more protrusion and slot fits provide precise alignment and orientation of two parts of an assembled implant.

The order and selection of steps in the manufacturing process is important to the successful use of hydration controlled interference fit. Some features such as aligned holes or surfaces are preferably created prior to a change in hydration state to preserve uniformity of critical dimensions across a portion or across a finished graft. In some cases it is advantageous to cut in the wet or hydrated state, assemble in the dry or dehydrated state, and then cut other features after assembly and swelling, with the whole graft in the hydrated state. In other cases, it is more efficient or reliable from the perspective of manufacturing flow to perform all machining steps during a single episode, then perform assembly and hydration in a second episode. Certain features such as outer profiles spanning two or more portions are preferably cut after assembly and rehydration to produce a reliable finish in the final implant.

Alternatively, in one preferred embodiment using natural bone materials with well understood material properties, two pieces are made separately and assembled in a later operation. In this embodiment, a mineralized cortical bone portion is machined to shape in a hydrated state, including a tapered undercut shaft cut to final dimensions which will produce the desired interference fit. This cortical bone portion is then demineralized and sterilized in a single procedure, all in a hydrated state. Following demineralization, the demineralized, sterilized portion of machined cortical bone is dehydrated under forced air flow, or by other suitable processes such as lyophilization. In a separate series of operations, a portion of mineralized cancellous bone is machined to shape in a hydrated state, including a tapered undercut bore cut to dimensions which will produce the desired interference fit, then sterilized. Following sterilization of the mineralized, sterilized portion of machined cancellous bone, the two bone portions are brought together for assembly, hydration and final packaging. The portions are assembled together with a clearance fit condition with the demineralized cortical bone in the dehydrated state, then the entire assembly is fully rehydrated resulting in a hydration controlled interference fit. In an optional variation of this preferred embodiment one of the bone portions, such as the cortical bone portion, is processed from two smaller equal pieces, with each of the two pieces making up about one half of the desired cortical bone portion including the tapered undercut shaft. This optional preferred embodiment has the advantage of making more bone material available for use by reducing the minimum size piece of bone suitable as a starting material.

In a preferred embodiment of the method of making the implants the cortical bone material is machined to shape in a hydrated state, then demineralized after machining by an aqueous or non-aqueous acid demineralization process, then dehydrated by forced air flow, lyophilization or other suitable method of dehydration, prior to final packaging and terminal sterilization in a package of two or more layers suitable for use in a surgical operating environment.

Lyophilization can be done with a lyophilizing machine until the bone is substantially free of moisture. Forced air drying can be done with any suitable source, such as a filtered, conditioned, sterile air supply found in many clean room environments. Lyophilization or forced air drying volatilizes residual processing chemicals, produces a more stable intermediate for storage and handling in-process, and follows pharmaceutical industry processing standards. Typically lyophilization results in a residual moisture content of about 10 weight percent or less, alternatively about 6 weight percent or less, alternatively about 3 weight percent or less, alternatively about 2 weight percent or less, alternatively about 1 weight percent or less.

Alternatively, bone is dried until a functional test condition is met, such as a reduction in dimension or an ability to fit into a certain hole, mating piece or test gage. For example, a bone portion having a shaft may be dried under forced air until such time as it will readily engage a mating piece having a bore under light hand pressure. Drying under forced air may be calibrated by time to dry, which varies according to temperature, relative humidity, and air flow rate. Typical drying times for some embodiments of the present implant portions may be at least about 30 minutes, preferably at least about 1 hour, more preferably about 60 to 90 minutes, also typically about 1 to 2 hours, alternatively more than about 2 hours. Actual drying times may be longer or shorter depending on implant portion design, processing conditions and airflow properties. Individual measurements or range limits may be combined to form new ranges. After the bone is dried, it can be stored in a manner that prevents rehydration from air moisture.

It is contemplated that the implants or assemblies are created outside the body of the intended recipient. This assembly outside the body has several advantages. The manufacturing process is separated from the surgical procedure, allowing for reduced cost and increased mechanisms for quality assurance and process control, thus resulting in safer, more economical and more reliable production of high quality grafts. The manufacturing process can be conducted using materials and equipment which may not be available or practical for use in the operating room environment. For example, it would be impractical if not impossible to completely dehydrate or demineralize an implant portion during a single operation to produce a graft suitable for implantation into that patient.

In an alternative embodiment, it is contemplated that the implants or assemblies are created in part outside the body of the intended recipient and prior to the surgical implantation, but fully realized or finalized during the surgical procedure or inside the body of the recipient. In one embodiment an implant is provided having a dehydrated demineralized cortical bone chondroinductive upper portion and a mineralized dehydrated cortical bone osteoconductive lower portion. The implant is delivered to the operating room in a sterile condition and free of any residual blood or lipids, in a kit including sterile packaging and instructions for use. The kit also optionally includes an insertion device compatible with arthroscopic or minimally invasive surgical technique. When this dehydrated implant is placed into the surgically created defect at the site in need of repair, the patient's own blood is drawn into the implant, rehydrating and swelling it while delivering native cells, nutrients and growth factors to support chondroinduction and healing. The implant is optionally further hydrated by directed application of blood, sterile water, or saline prior to implantation, or following implantation. The swelling action adds to any optional press fit or other fixation features and locks the lower portion in place, preferably within the patient's subchondral bone, at the surgically created defect site.

The use of appropriate manufacturing methods in the manufacturing process is important to the successful use of hydration controlled interference fit. In certain materials, such as bone, wet machining or cutting in the hydrated state, with or without the presence of excess liquid is preferred since bone is typically recovered and processed in a hydrated state and since wet or hydrated bone has natural lubricity which results in less chipping or breakage of the bone and improved surface finish condition. The natural lubricity of bone and the relatively moderate feed rates and spindle or cutter speeds employed in the machining of bone generally make additional lubricants or cooling fluids unnecessary, although sterile water, alcohol or saline may be used to remove debris from or to facilitate assembly of machined parts.

Dimensional changes due to changes in hydration state must be taken into account when machining bone. For this reason it is preferable in some cases to dry machine bone which will be assembled or shipped in a freeze dried or dehydrated state. The present implants are preferably stored and shipped in a hydrated state whenever a hydration controlled interference fit is employed.

An implant is chondroinductive when it induces the growth or formation of cartilage or other cartilaginous tissue. Factors known to contribute to chondroinductivity include presence of growth factors such as transforming growth factor-beta (TGF-beta), insulin-like growth factor (IGF), cartilage-derived morphogenetic proteins (CDMPs), and bone morphogenic proteins (BMPs). Additional factors contributing to chondroinductivity include cyclic compressive loading, hypoxic environment, surfaces that favor spherical as opposed to flattened cell configuration or surfaces that favor high cell density.

In some preferred embodiments, the chondroinductive implants exhibit stiffness and compliance similar to that found in natural articulating cartilage, and/or have the presence of some amount of chondroinductive growth factors, and/or have an internal structure and micro-structure of or similar to collagen which is supportive of cell migration, ingrowth and attachment, and/or have physical features such as canals or conduits which enhance or add mechanisms for cell, blood and fluid transport.

The static structural modulus (Young's Modulus) or stiffness of cartilage has been reported between about 0.5 MPa and 1 MPa. The stiffness of mineralized cortical bone is a highly anisotropic property, but has been reported between about 4 GPa and about 20 GPa. Demineralized bone matrix (DBM) pastes, gels or putties exhibit stiffness in the range of 0.1 MPa or less. In some preferred embodiments, the present implants comprise demineralized cortical bone material having a stiffness not more than about 1 GPa, alternatively not more than about 500 MPa, alternatively not more than about 100 MPa, alternatively not more than about 50 MPa, alternatively not more than about 10 MPa, alternatively not more than about 5 MPa, alternatively not more than about 2.5 MPa, alternatively not more than about 1.5 MPa, alternatively not more than about 1.0 MPa, alternatively not more than about 0.9 MPa, alternatively not more than about 0.8 MPa. Alternatively or additionally, the present implants comprise demineralized cortical bone material having a stiffness at least about 0.2 MPa, alternatively at least about 0.3 MPa, alternatively at least about 0.4 MPa, at least about 0.5 MPa, alternatively at least about 1 MPa, alternatively at least about 5 MPa, alternatively at least about 10 MPa, alternatively at least about 50 MPa, alternatively at least about 100 MPa, alternatively at least about 0.5 GPa. Any of the foregoing maximum and minimum stiffness values can be combined to form a range, so long as the maximum is greater than the minimum. For example, the present implants may comprise demineralized cortical bone material having a stiffness in the range between about 0.2 MPa and about 1 MPa, or even more preferably in one of the ranges between about 0.4 MPa and about 0.8 MPa, between about 0.5 MPa and about 1 MPa, between about 0.5 MPa and about 0.7 MPa, or between about 0.3 MPa and about 0.9 MPa. Thus the demineralized cortical bone material used in certain preferred embodiments of the present implants has a stiffness within the range of that known for native cartilage, while DBM pastes have a stiffness at least about one order of magnitude less than that found in native cartilage, and mineralized cortical bone has a stiffness at least about 4 orders of magnitude greater than that found in native cartilage.

The elastic modulus of mineralized cancellous bone, such as that found in the subchondral bone layer and as preferred for the osteoconductive base material of the present implants, is between about 2 GPa and about 4 GPa, typically about 3 GPa.

The chondroinductive implants have the capacity to stimulate or promote the formation of cartilage where such tissue otherwise would not form, such as by inducing the growth, maturation, reproduction or activity of chondrocytes, stem cells, fibroblasts, muscle cells or any other cells than cause or contribute to the formation of cartilage, thereby forming cartilaginous tissue. Due to the many diverse factors influencing chondroinductivity, the presence or absence of a single factor is not definitively predictive of chondroinductivity in-vivo. For example, isolated TGF-beta may be chondroinductive under a first set of conditions in-vivo or in-vitro, but may actually be non-inductive or osteoinductive under a second set of conditions in-vivo or in-vitro. The acceptable measure of chondroinductivity of an implant is an in-vivo model where the sample is implanted in an environment that does not spontaneously make cartilage, such as subcutaneously or in the abdomen muscle preferentially in the small size animals, like mice, rats or rabbits, Urist, M. R., "Bone: Formation by Autoinduction," Science 160:893-894 (1965). The chondroinductivity of the sample can then be assessed via histological and other analysis of the extent of cartilage formation in the in-vivo model.

The present implants differ in several important aspects from implants known for other purposes. When the implants include demineralized cortical bone as a chondroinductive element, the cortical bone element is demineralized sufficiently to prevent damage to adjacent articular cartilage surfaces and to allow natural bearing and dispersion of forces under anatomical loading conditions.

Embodiments of the present implants differ from known assembled bone grafts used in the spinal fusion implant or sports medicine and tendon fixation fields, where mineralized, lightly demineralized, or surface demineralized cortical bone constructs are used as osteoconductive or osteoinductive structural load bearing members. The preferred embodiments of the present implants have a relatively higher degree of demineralization and resulting lower modulus of elasticity and yield strength than spinal fusion implants or tendon fixation implants. Known implants for spinal fusion and tendon fixation would not serve as osteochondral implants, given their stiffness, roughness, and lack of compliance due to residual, substantial or total mineralization of the cortical bone elements.

Also in contrast to the present implants, demineralized bone matrix (DBM), as used in orthopedic applications, refers to a bone powder which is demineralized and mixed with graft material or a carrier such as gelatin, glycerol or a biocompatible polymer to form a non-load-bearing paste or putty composition. These DBM pastes differ from the osteochondral implants in the lack of ability of the DBM pastes to support anatomical loading in the joint space, their lack of ability to hold a preconfigured shape and/or maintain an assembly, and their lack of ability to support tissue regeneration in-vivo.

Synthetics, calcium compounds, ceramics, and polymers known in the art for use in other implants can be included in the present implants but are generally non-preferred due to their inferior regenerative and remodeling properties as compared to the preferred embodiments of the present implants, their lack of naturally occurring growth factors, and their inability to remodel into living tissues such as articular cartilage and subchondral bone. Although synthetics, calcium compounds, ceramics, and polymers may have growth factors or other agents added to them to promote chondroinductivity, the addition of a single growth factor or a small number of agents with demonstrated in-vitro chondroinductivity may not reliably produce chondroinductivity in-vivo.

Example 1

This example demonstrates a method of making an embodiment of an assembled implant.

Cancellous bone was obtained from the condyles of long bones, or optionally from the Talus or heel bone. The bone was cut into blanks with diameters ranging from roughly 6-13 mm and heights from 8-10 mm using a band saw and coring tools. The inner geometry of the cancellous bone was then machined using a dovetail cutter. A 1.5 mm hole was machined in the bottom center of the 8 mm and 10 mm cancellous bone portions. The cancellous bone portions are measured, inspected for quality, packaged, and stored frozen until processing for sterilization. The cancellous bone portions were sterilized, defatted and deantigenized, and soluble protein was removed by subjecting the cancellous tissue to cyclically alternating cycles of pressure and vacuum in the sequential presence of mild sterilizing chemical solutions. Following sterilization, the cancellous bone portions were packaged and stored until assembly with the cortical bone pieces or portions.

Cortical bone from a long bone shaft was cut into planks using a band saw. Bone planks were then cut into rectangular bone blanks measuring roughly 7-10 mm in height, 7-14 mm in width, and 7-8 mm in length using a band saw. Each blank was then machined to final dimensions such that the cortical bone portions have cap features with radii and negatively tapered shaft features with dovetails. The machined cortical bone portions were measured, inspected for quality, packaged, and stored until demineralization.

The surfaces of the cortical bone portions were decontaminated then thoroughly rinsed with water and demineralized by immersing them in USP Hydrochloric Acid (HCl), 1.0N (Thermo-Fisher) at an HCl volume to product volume ratio of at least 50:1. The container with cortical portions and acid was placed on a shaker and agitated. The cortical bone portions were then rinsed with phosphate buffered saline and then with water.

After the final water rinse, the cortical bone portions were ready to be assembled with the cancellous portions. The cortical bone portions were dehydrated by placing under forced air flow. The 8 mm portions were dehydrated for about 45 minutes, the 6 mm portions for about 60 minutes and the 10 mm portions for about 85 minutes, or until the cortical portions become small enough to fit inside the mating cancellous portion. The shaft of the single cortical bone portion (6 mm) or the combined assembled shafts of the two cortical bone portions (8 mm and 10 mm) were placed into the bore of the cancellous portion and the assembled implant was placed into a fixture designed to hold implants during rehydration. The implants were rehydrated using water for about 45 minutes or until the original cortical bone portion size and appearance had been restored. At this point, the implants were inspected for quality, packaged, and terminally sterilized.

Example 2

This example documents an animal study completed to confirm the chondroinductivity of an implant.

Prototype implants were implanted into an ectopic site in an athymic nude rat model, resulting in histologic evidence of chondroinduction without any signs of an inflammatory response.

Specifically, a 4 mm diameter by 2 mm tall disc taken from the demineralized cortical bone portion of Example 1 was implanted in abdominal muscle pouches of athymic nude rats using a modified Urist model, Urist, M. R., "Bone: Formation by Autoinduction," Science 160:893-894 (1965). The explants were retrieved two weeks later, processed, and evaluated histologically for evidence of new cartilage formation. The control implants made from chemically inactivated demineralized cortical bone material formed only fibrous material within the Haversian canals with minimal evidence of inflammation. More significantly, the implants made from active demineralized cortical bone demonstrated signs of chondrogenesis or new cartilage formation with minimal evidence of inflammation. Hence, the demineralized cortical bone matrix of the present invention provided both signaling and scaffolding for colonization by native restorative cells and the laying down of new cartilage.

Example 3

This example documents a cadaver study completed by a practicing surgeon experienced in cartilage repair at an orthopedic clinic to confirm the proper function and methods of use for the present implants.

Several primary-site implants were made to production specifications using an assembled biological implant comprising a two piece chondroinductive demineralized cortical bone cap assembled via a hydration controlled interference fit to a mineralized cancellous bone osteoconductive portion. The assembled implants were implanted into a cadaver knee using an open approach. The implants were left out at room temperature for several minutes and were then placed in room temperature saline for a minimum of ten minutes to ensure consistent final levels of hydration prior to implantation. The surgeon prepared the implantation site by coring out an 8 mm diameter plug from the primary site using an OATS single-use kit. He measured the depth of the defect using the depth gauge and verified that it was between 9 mm and 10 mm, as the plug height is 10 mm. He then loaded the assembled implant into the 8 mm diameter delivery tube such that the cancellous portion of the implant was toward the bottom (so it would fill the cancellous portion of the defect) and the demineralized bone portion was on the top (so it would be congruent with the articulating surface). He aligned the delivery tube with the defect site and tamped the implant into the void. The implant was almost completely implanted, and at this point he removed the delivery tube and completed pushing the implant into the site using a surgical tamp and mallet. Once the implant was flush with the articulating surface, the implantation was complete.

The surgeon then proceeded to implant a 10 mm implant in the same fashion, followed by a 6 mm implant in a "snowman" configuration with the 10 mm implant. This was achieved by coring out a second 6 mm defect that overlapped with ⅓ of the first installed 10 mm implant, resulting in an overlapping, non-coaxial, non-uniformly sized multiple implant configuration resembling the profile of a snowman. After coring the 6 mm defect, he inserted the 6 mm implant using the delivery tube. The 10 mm implant was slightly more depressed than the 6 mm implant in its final position, which was a result of the second implant pushing it down as it was implanted. It was recommended that when using the snowman technique, the first implant be inserted to a depth of only about 8 to 8.5 mm so that it has room to subside during implantation of the second implant.

The final implantation was a 10 mm implant into a widened 8 mm defect. This was done to determine robustness of the implant to situations where an 8 mm defect was widened during surgery to the extent that the 8 mm implant would no longer fill the void. The 10 mm implant fit well into the widened 8 mm hole.

Example 4

This example documents a cadaver study to confirm the proper function and methods of use for several implants.

Eighteen assembled bifunctional biological implants were evaluated in a simulated use environment to validate the design against user needs.

Primary site and backfill implants, sizes 6 mm, 8 mm, and 10 mm, were evaluated by implanting into a cadaver knee using an open, non-arthroscopic technique.

Prior to implantation, the interface of the implants with their appropriate delivery devices was evaluated. The implants were placed into the instruments and each instrument was held vertically so that the end with the implant was facing upwards. The instrument was inverted so that the implant end was facing the floor. This was repeated five times to demonstrate that the implants do not fall out of the instrument during normal movement. In addition, the plungers for the instruments were used to push the implants out of the tube, as would be done during implantation. The implants did not become stuck in the tube. These tests demonstrated that the implant's outer diameter dimensions are sufficient to interface with the appropriate instrumentation.

The implant was then evaluated to determine whether it was robust enough to maintain integrity during typical manipulations. The cancellous end of the implant was trimmed 2 mm as might be done prior to implantation if the surgeon cored out a shallow defect. The implants did not crack, chip, break, or come apart, demonstrating that they could withstand normal manipulations.

To prepare for the implantation, primary and backfill sites were prepared by coring out appropriately sized defects using an OATS single-use kit. One defect of each primary size was cored on the primary sites of each femoral condyle, and one defect of each backfill size was cored on the edges of the condyles, which are typical sites for obtaining autologous plugs. The depth of each defect was measured using the depth gauge and it was verified that each was between 9 mm and 10 mm. The implants were loaded into the delivery devices such that the cancellous portion of the implants were toward the bottom (so they would fill the cancellous portion of the defect) and the demineralized bone portion was on the top (so they would be congruent with the articulating surface). For each implantation, the delivery tube was aligned with the defect site and tamped into the void. Tamping continued until the implants were flush with the articulating surface.

After implantations were complete, the implants were inspected for integrity. The articulating surfaces of the implants were in their original conformations and without chips or cracks. The demineralized bone portions were firmly attached to the cancellous portions.

The performance of the implanted implants was evaluated by marking the position of the implants and then manually cycling the knees from 90° flexion to full extension at a rate of about two cycles per second. The knees were cycled 30 times. After cycling, the implants were examined. None had rotated or moved vertically out of position.

Example 5

This example demonstrates a method of using an embodiment of an assembled bifunctional biological implant for backfilling a secondary site created during an autograft cartilage repair procedure in a human patient (e.g. OATS procedure).

The primary site lesion is identified and cored or drilled out using appropriate instrumentation. A similarly-sized autograft cartilage plug is cored out from a relatively non load-bearing area of the same condyle using appropriate instrumentation. The autograft plug is then inserted into the void at the primary site.

The result from obtaining the autograft plug is a cylindrical void or surgically created defect in the cartilage and underlying bone. The depth of the void is measured using a depth gauge. The depth gauge serves to measure depth as well as compact any debris in the void. The depth of the void is made to be approximately 9-10 mm, and preferably about 9.8 mm for insertion of a 10 mm graft. The slightly undersized depth allows for compaction and reduction of any voids at the base of the implant while resulting in a flush and not recessed final height of the implant. An assembled implant with a similar diameter to the void is chosen. The graft is loaded into a delivery device (tube with an inner diameter that is similar to the diameter of the graft) such that following placement the cancellous portion will fill the bottom of the void and the demineralized portion will be visible on the surface of the condyle. The end of the tube holding the graft is aligned with and mated to the void. A rod with a similar diameter as the graft is inserted into the tube and tamped against the graft using a surgical mallet, pushing the graft into place. The rod may be tamped with force to push the graft into position. When all of the cancellous portion and at least half of the demineralized portion of the graft are implanted, the tube and rod are removed. The graft is pushed further into the void using a standard surgical tamp and mallet. Once the graft is flush with the surface and no protrusions remain, the implantation is complete.

Example 6

This example demonstrates a method of using an embodiment of an assembled bifunctional biological implant for repairing a primary site defect in a human patient.

The primary site lesion is identified and cored or drilled out using appropriate instrumentation. The depth of the resulting void is measured using a depth gauge. The depth gauge serves to measure depth as well as compact any debris in the void. The depth of the void is made to be approximately 9-10 mm. An assembled implant with a similar diameter to the void is chosen. The implant may be the same size as the void, slightly undersized or slightly oversized in either height or diameter, depending on surgeon preference. Typically the implant is slightly oversized in both height and diameter for the void it is filling, resulting in a light press fit and slight compaction of the implant upon full depth insertion. The implant is loaded into a delivery device (tube with an inner diameter that is similar to the diameter of the implant) such that upon insertion the cancellous portion will fill the bottom of the void and the demineralized portion will be visible on the surface. The end of the tube holding the implant is aligned with and mated to the void. A rod with a similar diameter as the implant is inserted into the tube and tamped against the implant using a surgical mallet, pushing the implant into place. The rod may be tamped with force to push the implant into position. When all of the cancellous portion and at least half of the demineralized portion of the implant are implanted, the tube and rod are removed. The implant is pushed further into the void using a standard surgical tamp and mallet. Once the implant is flush with the surface and no protrusions remain, the implantation is complete.

Example 7

This example demonstrates a surgical technique guide for a method of using an embodiment of an assembled bifunctional biological implant for repairing a primary site defect in a human patient.

Identify the primary site lesion and remove damaged cartilage and debris until the edges of the defect site are composed of healthy cartilage.

Determine the size of the lesion and decide how many assembled implants will be needed and in what sizes. If multiple implants are needed, decide whether the implants will be placed next to one another or overlapping. Plan to overlap implants by no more than ⅓.

Remove the implants from the packaging and allow to them to hydrate in room temperature water or saline.

Using appropriate instrumentation, core or drill the defect using 6 mm, 8 mm, or 10 mm diameter instruments. Use the smallest diameter possible that removes all damaged cartilage.

Measure the depth of the cored defect using a depth gauge. Use the depth gauge to compress debris at the bottom of the defect. Ensure that the defect is 9.0-9.8 mm deep and that the bottom of the defect is parallel with the surface of the articulating cartilage. If the defect is too shallow, deepen the site by impacting the depth gauge with a mallet. If the defect site is too deep, add cancellous bone from the cored material.

Place the assembled implant into the delivery device such that the cancellous portion is visible on the implanting end of the tube. This results in the cancellous portion being implanted at the bottom of the site (congruent with the native cancellous) and the demineralized cortical bone remaining at the surface of the defect (congruent with native cartilage).

Align the opening of the delivery device with the defect. Guide the implant into the defect by pushing on the rod. When the implant does not easily slide into the defect site, use a mallet to impact the rod, pushing the implant into position. Ensure that the delivery device remains perpendicular to the surface of the articulating cartilage to avoid widening the defect site or implanting the implant at an angle.

Once all of the cancellous portion is implanted and at least about half of the demineralized bone portion is implanted below the articulating cartilage surface, the delivery tube may be removed (if desired) and the wide end of the delivery device or a surgical tamp and mallet may be used directly on the surface of the implant. Impact the surface of the implant until it is completely flush with the surface of the articulating cartilage. Do not leave portions of the implant protruding above the surface.

If additional implants are needed and are going to be implanted next to one another, a similar technique as for the first implant should be followed.

If additional implants are needed and are going to be implanted in an overlapping configuration, certain modifications to the technique are desirable.

When implanting the first implant of an overlapping multiple implant configuration, make the initial defect 8.0-8.5 mm deep. This will prevent the implant from subsiding when the second implant slides down next to it.

When implanting the first implant of an overlapping multiple implant configuration (a "snowman" configuration), ensure that the implant is oriented such that the seam or set of mating surfaces between the two assembled demineralized cortical cap pieces (if the implant's demineralized cortical bone cap portion is assembled from two pieces of cortical bone) is perpendicular to (or points to) the planned site of the second implant. About ⅓ of the first implant will be cored out, and coring out evenly across the two assembled demineralized cortical bone cap pieces will minimize stress on the first implant during implantation of the second implant.

When coring the site for the second implant, core out no more than about ⅓ of the first implant.

When implanting the second implant, the first implant will subside even though it is not being directly impacted. However, it may still be slightly proud when both implants are implanted. To complete the procedure, tamp on both implants to ensure both implants are flush with the native cartilage.

In the present specification, use of the singular includes the plural except where specifically indicated. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (meaning "including, but not limited to,") unless otherwise noted. Whenever the term "about" appears before a value, it should be understood that the specification is also providing a description of that value apart from the term "about". Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In the present specification, any of the functions recited herein may be performed by one or more means for performing such functions. With respect to the methods described in the specification, it is intended that the specification also provides a description of the products of those methods. With respect to the compositions and combinations described in the specification, it is intended that the specification also provides a description of the components, parts, portions, of such compositions and combinations.

All of the references cited herein, including patents, patent applications, and publications, are hereby incorporated in their entireties by reference.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

Although the dependent claims have single dependencies in accordance with U.S. patent practice, each of the features in any of the dependent claims can be combined with each of the features of other dependent claims or the main claim.

The invention claimed is:

1. A bifunctional assembled implant adapted for implantation at a non-load bearing site of a bone cartilage junction, comprising:
   an osteoconductive portion, comprising cancellous bone, adapted to fill a defect in a subchondral bone layer; and
   a chondroinductive portion, comprising fully demineralized cortical bone, adapted to fill a cartilage layer adjacent to the subchondral bone layer;
   wherein said osteoconductive portion and said chondroinductive portion are assembled in a stacked relationship without separate fasteners or adhesives;
   wherein said osteoconductive portion and said chondroinductive portion each defines a characteristic depth and a characteristic width; and wherein said characteristic depth of said osteoconductive portion is substantially equivalent to or greater than said characteristic depth of said chondroinductive portion; and
   wherein said osteoconductive portion and said chondroinductive portion are assembled to have an interference fit; and
   wherein said implant is adapted to backfill a secondary site created during an autograft cartilage repair procedure in a human patient.

2. The implant of claim 1, wherein said characteristic depth of said osteoconductive portion is at least about one and one half times greater than said characteristic depth of said chondroinductive portion; and wherein said characteristic width of said osteoconductive portion is substantially the same as said characteristic width of said chondroinductive portion.

3. The implant of claim 1, wherein said interference fit is a hydration controlled shrink fit.

4. The implant of claim 1, wherein said interference fit further comprises a shaft and bore fit between said osteoconductive portion and said chondroinductive portion, and the shaft is straight or tapered.

5. The implant of claim 1, wherein said chondroinductive portion comprises from two to eight pieces of cortical bone.

6. The implant of claim 5, wherein said chondroinductive portion comprises two pieces of cortical bone.

7. The implant of claim 6, wherein said two pieces of cortical bone each make up about one half of said chondroinductive portion.

8. The implant of claim 1, wherein said osteoconductive portion substantially surrounds at least one part of said chondroinductive portion.

9. The implant of claim 1, wherein said chondroinductive portion comprises allograft bone, xenograft bone, or a combination thereof.

10. The implant of claim 1, wherein said cortical bone material further includes one or more canals, said canals being oriented in a direction providing transport between said cancellous bone and said cortical bone.

11. A method of using an assembled osteochondral implant, comprising filling a defect site with said bifunctional assembled implant of claim 1, such that a first region of said defect site is filled by osteoconductive cancellous bone material and a second region of said defect site is filled by chondroinductive cortical bone material.

* * * * *